US008191566B2

(12) United States Patent
Donahue

(10) Patent No.: US 8,191,566 B2
(45) Date of Patent: Jun. 5, 2012

(54) VALVE FOR CONTROLLING THE FLOW OF STEAM AND OTHER FLUIDS

(75) Inventor: John Donahue, Kirkland, WA (US)

(73) Assignee: AMGEN Inc., Thousand Oaks, CA (US)

( * ) Notice: Subject to any disclaimer, the term of this patent is extended or adjusted under 35 U.S.C. 154(b) by 597 days.

(21) Appl. No.: 12/355,663

(22) Filed: Jan. 16, 2009

(65) Prior Publication Data

US 2009/0120503 A1 May 14, 2009

Related U.S. Application Data

(63) Continuation-in-part of application No. PCT/US2007/016428, filed on Jul. 20, 2007.

(60) Provisional application No. 60/832,446, filed on Jul. 21, 2006.

(51) Int. Cl.
*F16K 17/40* (2006.01)
*A61L 2/07* (2006.01)
(52) U.S. Cl. .................. 137/68.23; 137/241; 422/26
(58) Field of Classification Search ............... 137/68.19, 137/68.23, 68.24, 68.25, 68.27, 241; 251/4; 220/89.2; 422/26
See application file for complete search history.

(56) References Cited

U.S. PATENT DOCUMENTS

| 1,485,913 | A | 3/1924 | Gottlieb |
| 1,667,141 | A | 4/1928 | Crowley |
| 1,959,822 | A | 5/1934 | Greve |
| 2,092,925 | A | 9/1937 | Lithgow |
| 2,553,267 | A | 5/1951 | Nedoh |
| 3,131,033 | A * | 4/1964 | Van Volkenburgh ....... 137/68.23 |
| 3,445,032 | A | 5/1969 | Raid, Jr. et al. |
| 3,845,879 | A | 11/1974 | Dernbach et al. |
| 3,881,629 | A | 5/1975 | Shaw et al. |
| 4,064,003 | A | 12/1977 | Newton |
| 4,441,350 | A | 4/1984 | Short, III et al. |
| 4,458,516 | A | 7/1984 | Naumann |
| 5,063,958 | A | 11/1991 | Wisneskie et al. |
| 5,167,337 | A | 12/1992 | Short, III et al. |
| 5,172,956 | A | 12/1992 | Klose et al. |
| 5,265,652 | A | 11/1993 | Brunella |

(Continued)

FOREIGN PATENT DOCUMENTS

| WO | 0390843 | 11/2003 |
| WO | 2008011132 | 1/2008 |

OTHER PUBLICATIONS

Colder Products Company®, Steam-Thru Connections Features & Benefits webpage, 2005 <http://www.colder.com/asp_main/FeaturesBenefits/SteamThruFBBio.asp>, Mar. 6, 2006. Millipore Catalogue—Lynx ST Connector for Steam-to Connection webpage, 2006 <http://www.millipore.com/catalogue.nsf/docs/C9131>, Mar. 6, 2006.

(Continued)

*Primary Examiner* — John Rivell
(74) *Attorney, Agent, or Firm* — Christensen O'Connor Johnson Kindness PLLC

(57) ABSTRACT

Systems (e.g., bioprocessing systems), including methods and apparatus, for controlling the flow of a sterilizing agent (e.g., steam) and/or at least one fluid reagent by utilizing a pressure-responsive valve, such as a rupture valve and/or a swing valve.

20 Claims, 9 Drawing Sheets

U.S. PATENT DOCUMENTS

| | | |
|---|---|---|
| 5,411,158 A | 5/1995 | Kays et al. |
| 6,192,914 B1 | 2/2001 | Farwell |
| 6,491,109 B2 | 12/2002 | Christenson et al. |
| 6,983,758 B2 | 1/2006 | DeCourcy et al. |
| 7,004,187 B2 | 2/2006 | Hoffman |
| 2005/0016620 A1 | 1/2005 | Proulx et al. |

OTHER PUBLICATIONS

Rivell, John, Authorized officer, International Searching Authority, International Search Report, International Application Serial No. PCT/US2007/016428; search date: Jun. 6, 2008.

* cited by examiner

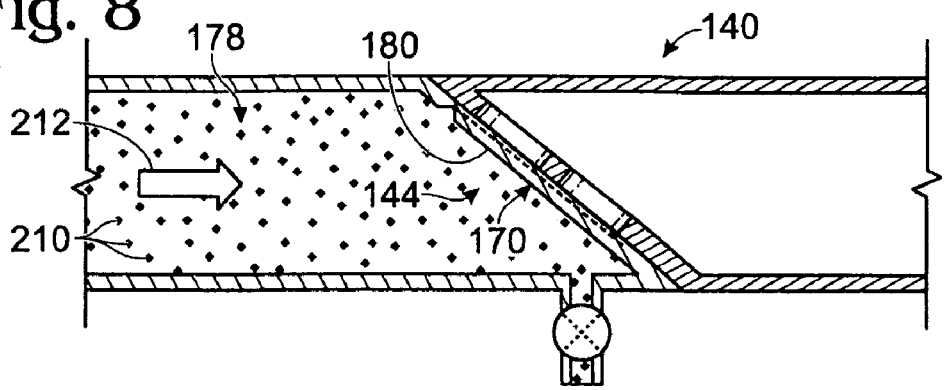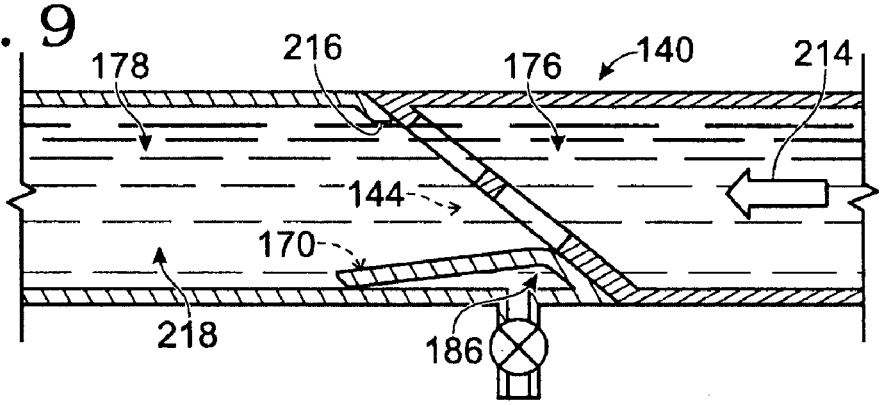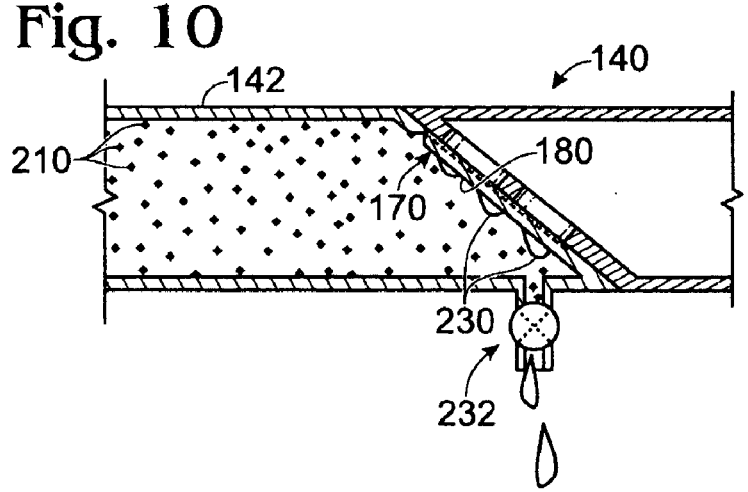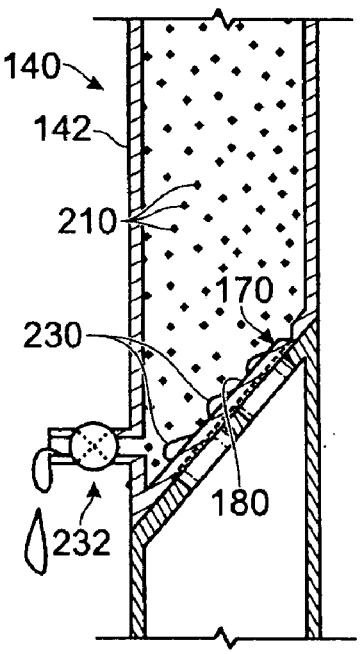

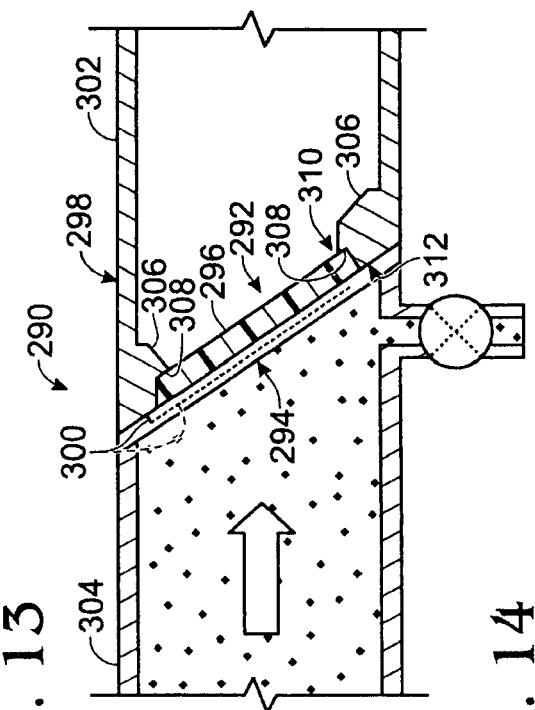
Fig. 13
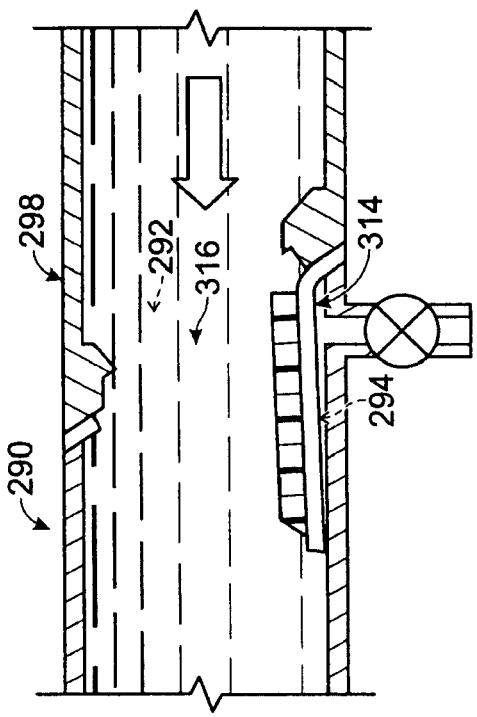
Fig. 14
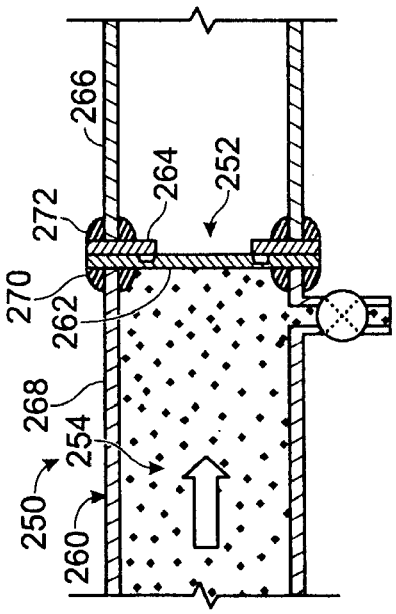
Fig. 12
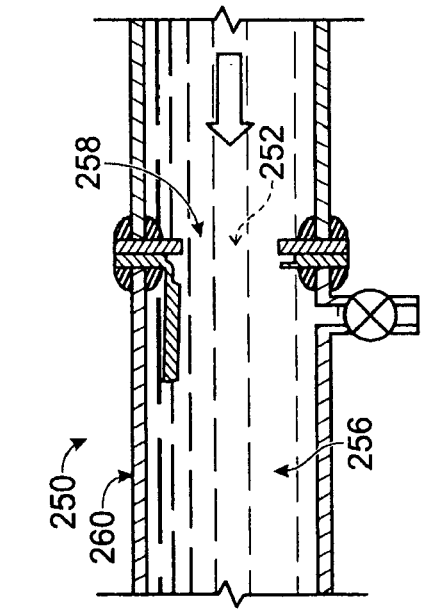

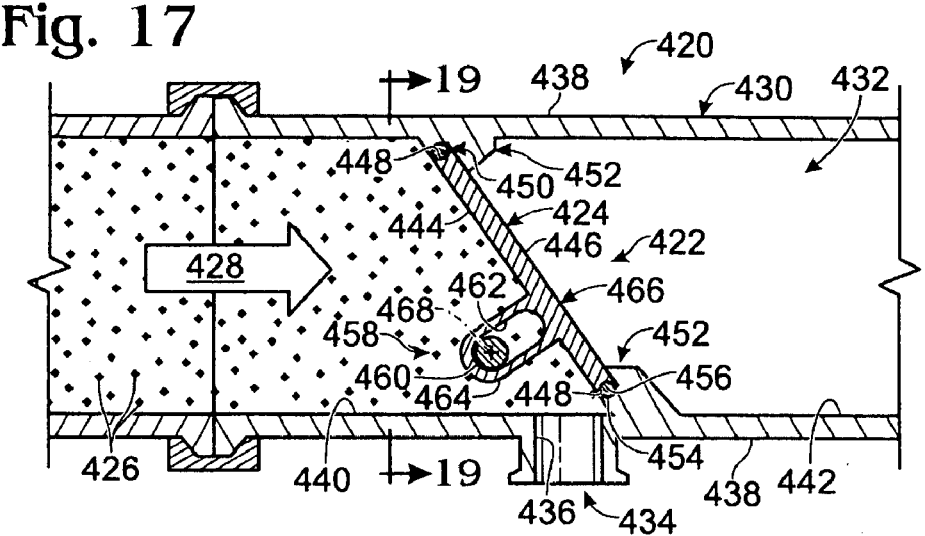
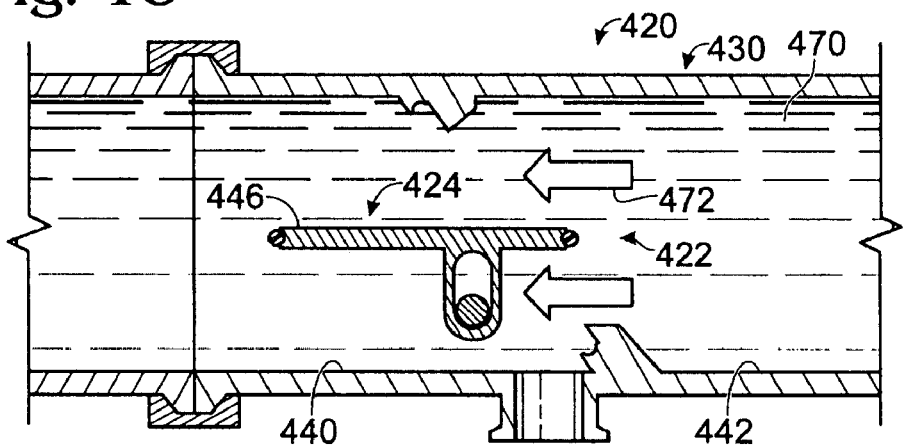
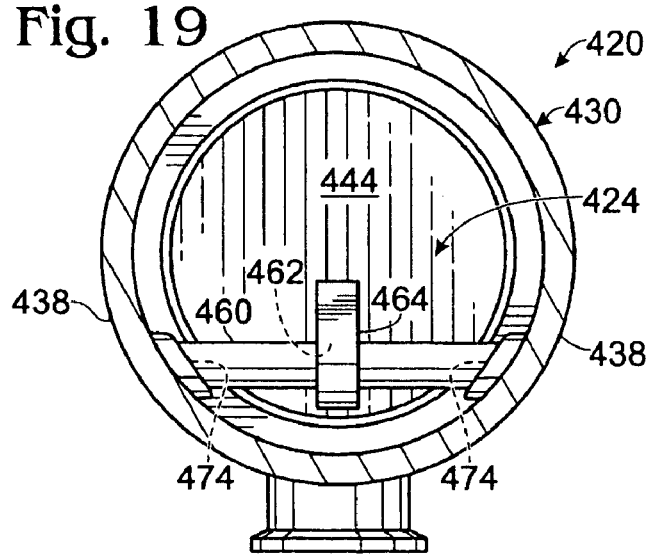

VALVE FOR CONTROLLING THE FLOW OF STEAM AND OTHER FLUIDS

CROSS-REFERENCES TO RELATED APPLICATIONS

This application is a continuation-in-part of PCT Patent Application Serial No. PCT/US2007/016428, filed Jul. 20, 2007, and published Jan. 24, 2008, as WO2008/011132, which in turn claimed the priority of U.S. Provisional Patent Application No. 60/832,446, filed Jul. 21, 2006. These two priority applications are incorporated herein by reference in their entireties for all purposes.

INTRODUCTION

Process vessels, such as bioreactors, may provide a substantially closed environment for creating mixtures, performing chemical reactions, and/or growing biological cells, among others. For example, bioreactors often are employed to produce pharmaceuticals from engineered cells grown in many liters of culture media. In some cases, the cells placed into a bioreactor may be mammalian cells that grow more slowly than potential sources of contamination, such as bacteria and fungi. In any event, effective sterilization of a process vessel, and of fluid reagents introduced into the process vessel, may be fundamental to the successful use of the process vessel without interference from unwanted microorganisms.

Small devices and vessels, due to their portability, may be placed into a chamber and sterilized via gamma irradiation, autoclaving, or other means in the chamber. Larger process vessels and devices, on the other hand, due to their lack of portability, typically are sterilized using "steam-in-place" (SIP) sterilization. SIP sterilization of a process vessel generally involves connecting the process vessel to a steam source, such as via a conduit(s) and valve(s), to expose the interior volume and interior surfaces of the process vessel to the lethal effect of steam without the need to move the process vessel. Furthermore, SIP sterilization may be performed repeatedly as different fluid sources are connected to the process vessel. However, the conduit(s) and valve(s) used in connecting the process vessel to the fluid sources may require cleaning and/or re-sterilization between uses, which may be costly and time consuming. Accordingly, new approaches for controlling steam application and transfer of fluids to and from process vessels after steam application would be beneficial.

SUMMARY

The present teachings provide systems (e.g., bioprocessing systems), including methods and apparatus, for controlling the flow of a sterilizing agent (e.g., steam) and/or at least one fluid reagent by utilizing a pressure-responsive valve, such as a rupture valve and/or a swing valve.

BRIEF DESCRIPTION OF THE DRAWINGS

FIG. 8 is a fragmentary, longitudinal sectional view of the conduit assembly of FIG. 5 taken during selective application of steam to an outlet portion of the conduit assembly, in accordance with aspects of the present teachings.

FIG. 9 is a fragmentary, longitudinal sectional view of the conduit assembly of FIG. 5 taken after rupture of the rupture valve as fluid flows through a passage created by valve rupture, from an inlet portion to an outlet portion of the conduit assembly, in accordance with aspects of the present teachings.

FIGS. 10 and 11 are fragmentary, longitudinal sectional views of the conduit assembly of FIG. 5, taken as in FIG. 8 during application of steam, with the conduit assembly disposed in respective horizontal and vertical orientations and with steam condensate traveling along an oblique surface of the rupture valve to a drain valve, in accordance with aspects of present teachings.

FIG. 12 is a pair of fragmentary, longitudinal sectional views of another exemplary conduit assembly taken respectively before and after rupture of a rupture valve of the conduit assembly, in accordance with aspects of the present teachings.

FIG. 13 is a fragmentary, longitudinal sectional view of yet another exemplary conduit assembly taken during selective application of steam to an outlet portion of the conduit assembly, in accordance with aspects of the present teachings.

FIG. 14 is a fragmentary, longitudinal sectional view of the conduit assembly of FIG. 13 taken after rupture of a rupture valve of the conduit assembly and as fluid flows through the conduit assembly, in accordance with aspects of the present teachings.

FIG. 17 is a fragmentary, longitudinal sectional view of an exemplary conduit assembly during steam-in-place sterilization, with the conduit assembly including a swing valve in a closed configuration that blocks fluid flow through the swing valve and conduit assembly, in accordance with aspects of the present teachings.

FIG. 18 is a fragmentary, longitudinal sectional view of the conduit assembly of FIG. 17, with the swing valve in an open FIG. 19 is a sectional view of the conduit assembly of FIG. 17, taken generally along line 19-19 of FIG. 17 toward the swing valve.

DETAILED DESCRIPTION

Figure 1:
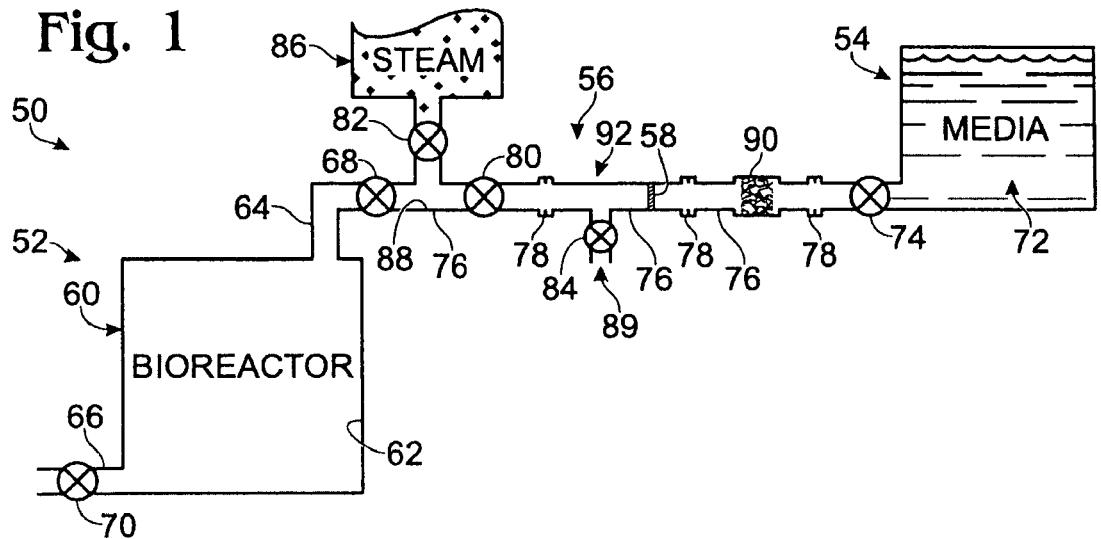
FIG. 1 is a schematic view of an exemplary bioprocessing system including a pressure-responsive valve for controlling steam application and fluid flow, in accordance with aspects of the present teachings.

The present teachings provide systems (e.g., bioprocessing systems), including methods and apparatus, for controlling the flow of a sterilizing agent (e.g., steam) and/or at least one fluid reagent by utilizing a pressure-responsive valve, such as a rupture valve and/or a swing valve. In some embodiments, the valve may restrict fluid flow to control application of steam and/or to maintain sterility upstream and/or downstream of the valve.

The apparatus may include a conduit assembly with a conduit occluded by a pressure-responsive valve. The valve may operate like a check valve that opens (e.g., ruptures and/or swings) selectively in response to pressure exerted by fluid and/or by an actuator on one of two opposing sides of the valve, such as pressure exerted generally in one of two opposing (potential) flow directions through the conduit. For example, the valve may have opposing sides (which may be termed faces) and may open or be openable selectively with pressure exerted on one side or face of the valve relative to the other side or face of the valve. Accordingly, the valve may restrict fluid flow past the valve, such as during steam-in-place sterilization. In addition, the valve may open after the sterilization, in response to pressure on the valve, to permit fluid flow through the valve, such as for addition of a fluid reagent(s) to a connected vessel (e.g., a reaction chamber of a bioreactor).

In some embodiments, the valve may be a rupture valve incorporating any suitable features. In some embodiments, the rupture valve may be disposed obliquely in the conduit. An oblique disposition of a rupture valve may, in some cases, facilitate removal of steam condensate from the conduit assembly in both horizontal and vertical orientations of the conduit. In some embodiments, the rupture valve may include a rupturable occlusion element and a support element connected in a face-to-face relationship with one another. The support element may support the rupturable element during the exertion of upstream-directed pressure on the rupture valve (such as during application of steam), and then may pivot with the rupturable element when the rupturable element bursts.

In some embodiments, the valve may include a discrete disc that blocks fluid flow through the conduit and that divides a channel of the conduit into first and second portions. The disc may be coupled pivotably to the conduit and disposed in a sealed connection with the conduit, the disc may have opposing faces and may pivot (or swing) to provide an open configuration of the valve selectively in response to pressure exerted on one of the opposing faces from the first portion of the channel relative to pressure exerted on the other opposing face from the second portion of the channel.

In some embodiments, the valve may be operatively coupled to an actuator adjacent one of the opposing faces of the valve. The actuator may have a sealed connection to the conduit. The actuator may be accessible outside the conduit to permit a user to exert pressure on the one opposing face via the actuator, to place the valve in an open configuration manually. In some examples, the actuator may lock to the conduit, which in turn may lock the valve in an open configuration. Furthermore, the actuator may be connected to the conduit with a web to form the sealed connection between the actuator and the conduit. The actuator may include a brace member that locks to the conduit over the web in an open configuration of the valve.

In some embodiments, the valve may be locked in a closed configuration using a detent member, which may engage a face of the valve. The detent member may be removed, such as from an end of the conduit, or otherwise disengaged before use of the valve. In some examples, the detent member may be removed from an end of the conduit, and then replaced by a connection to another conduit. In some examples, the conduit assembly may include a filter and a lateral port disposed between the filter and the valve. The lateral port may be utilized to permit fluid flow through the filter and out of the conduit during integrity testing of the filter, with the valve locked in the closed configuration.

The apparatus may be connected to an upstream (and/or downstream) device such as a capsule filter, tubing assembly, or small vessel, among others, and sterilized while connected to the upstream device (e.g., via gamma-irradiation, autoclaving, etc.). The valve, when closed, may ensure that the connected device remains sterile prior to use and/or prior to connection to a process vessel. Accordingly, the valve may allow an upstream device to be connected aseptically to a process vessel.

The present teachings provide a method of fluid transfer. A conduit assembly may be selected. The conduit assembly may include a conduit and a valve, such as a rupture valve, dividing a channel of the conduit into a first or inlet portion and a second or outlet portion. The valve may have opposing first and second faces that respectively adjoin the first/inlet portion and the second/outlet portion. The valve may be selectively opened (e.g., ruptured) in response to pressure exerted on the valve (and/or on the first face) from the first/inlet portion relative to pressure exerted on the valve (and/or on the second face) from the second/outlet portion. A sterilizing agent, such as steam, may be applied to the second/outlet portion of the conduit with the rupture valve restricting entry of the sterilizing agent into the first/inlet portion. The valve may be opened (e.g., ruptured) with pressure exerted on the valve (and/or the first face) from the first/inlet portion, which may create a passageway through the rupture valve. In some examples, fluid, such a fluid reagent, may be flowed through the passageway of the rupture valve. In some examples, a fluid reagent, which may be substantially liquid, may be added to a receiver vessel connected to the conduit assembly, from a supply vessel containing the fluid reagent and through the passageway of the rupture valve In some examples, the conduit assembly may include a main conduit and an ancillary conduit that branches from the main conduit, with the main conduit being divided by the valve. Steam condensate may be removed from the main conduit via the ancillary conduit during the step of applying steam. The method of fluid transfer also or alternatively may be performed with any of the other conduit assemblies provided by the present teachings and/or any combination of features thereof.

Overall, the systems of the present teachings may provide substantial advantages over other systems employing more complicated mechanical valves for maintaining sterility and regulating fluid flow before, during, and/or after sterilization in-place. These advantages may include, for example, greater flow rates, disposability, lower overall cost, and/or reduced microbial contamination, among others.

Further aspects of the present teachings are described in the following sections, including, (I) overview of an exemplary bioprocessing system; (II) conduit assemblies, including (A) conduits, (B) pressure-responsive valves, (C) and drains; (III) methods of making conduit assemblies; (IV) methods of using conduits assemblies; and (V) examples.

I. OVERVIEW OF AN EXEMPLARY BIOPROCESSING SYSTEM

The valves of the present teachings may be used in any suitable system in which fluid is being transferred within, into, and/or out of the system. In particular, the valves may be appropriate for systems that benefit from sterile conditions, such as bioprocessing systems. This section describes exemplary configurations of a bioprocessing system with a valve.

FIG. 1 shows an exemplary bioprocessing system 50. System 50 may include a downstream receiver vessel 52 connected to an upstream supply vessel 54 by a fluid conduction subsystem (an addition assembly) 56 that includes at least one valve 58, such as a rupture valve and/or a swing valve. The valve may regulate fluid flow through the conduction subsystem by, for example, restricting reverse (upstream) flow (receiver vessel 52 to supply vessel 54) during sterilization and permitting forward (downstream) flow (supply vessel 54 to receiver vessel 52) afterwards. More generally, the valve may remain closed (e.g., may resist rupture) with a substantial pressure drop directed upstream on the valve and may open (e.g., may rupture) with the same substantial pressure drop directed downstream on the valve.

The receiver vessel may be a process vessel for performing bioprocessing, such as growth of cells, production of biological products, enzymatic reactions, and/or the like. Accordingly, the receiver vessel may be a closed container (here, a bioreactor 60) defining a reaction chamber 62. In addition, the receiver vessel may have an inlet region(s) 64 at which the receiver vessel connects to the fluid conduction subsystem and an outlet region(s) 66 for removing fluid from the bioreactor (such as during and/or after bioprocessing and/or to remove steam condensate (see below)). Fluid entry into and/or out of the receiver vessel may be controlled by valves, such as an inlet valve 68 and an outlet valve 70, respectively.

Supply vessel 54 (which may be termed a source vessel) may serve as a fluid source that contains a fluid reagent 72 (here, media) prior to delivery of the fluid reagent to the fluid conduction subsystem and then the bioreactor. The source vessel may be open, or may be a closed container as shown here. Entry of the fluid reagent into fluid conduction subsystem 56 may be regulated by an outlet valve 74, may be facilitated by a vent, and/or may be driven by a pump, among others.

Fluid conduction subsystem 56 may direct and regulate the flow of fluid between the source vessel and the receiver vessel. Subsystem 56 thus may include one or more conduits 76, connected to one another and/or to the supply and/or receiver vessels via couplings 78, and one or more in-line valves 80 and/or branch valves 82, 84. The branch valves may function as ports to introduce fluid into and/or out of the conduction subsystem. For example, valve 82 may be configured to regulate fluid communication between a steam source 86 and a main channel 88 of the conduction subsystem, for application of steam to the main channel and/or bioreactor. In contrast, drain valve 84 (also termed a bleed valve) may provide removal of fluid from the system via a drain 89, such as removal of condensate that accumulates during steam sterilization.

The fluid conduction subsystem also may alter and/or sense fluid as it travels through the conduction subsystem. For example, the conduction subsystem may have a filter 90 and/or other fluid modification and/or sensing devices (such as mixers, heaters, coolers, degassers, electrodes, temperature sensors, flow sensors, fluid sensors, pH sensors, position sensors, and/or the like).

Valve 58 may be included in the bioprocessing system as part of a conduit assembly 92. The conduit assembly may form at least part of the main channel of the fluid conduction subsystem and thus may have coupling structures 78 that permit the conduit assembly to be integrated into the conduction subsystem. In addition, the conduit assembly may include drain valve 84, filter 90, and/or other accessory devices, structures, and/or features as described elsewhere in the present teachings. Filter 90 and valve 58 (and any suitable portion of fluid conduction subsystem 56) may be connected (or formed as a unit) and then sterilized as a unit via autoclaving, gamma irradiation, or other suitable means, prior to incorporating the unit into the system. In other embodiments, supply vessel 54, an intervening portion of fluid conduction subsystem 56, and valve 58 (with or without filter 90) may be connected (or formed as a unit) and then sterilized as a unit via autoclaving, gamma irradiation, or other suitable means, prior to incorporating the unit into the system. Further structural aspects of conduit assemblies are described below, for example, in Sections II and V.

Figure 2:
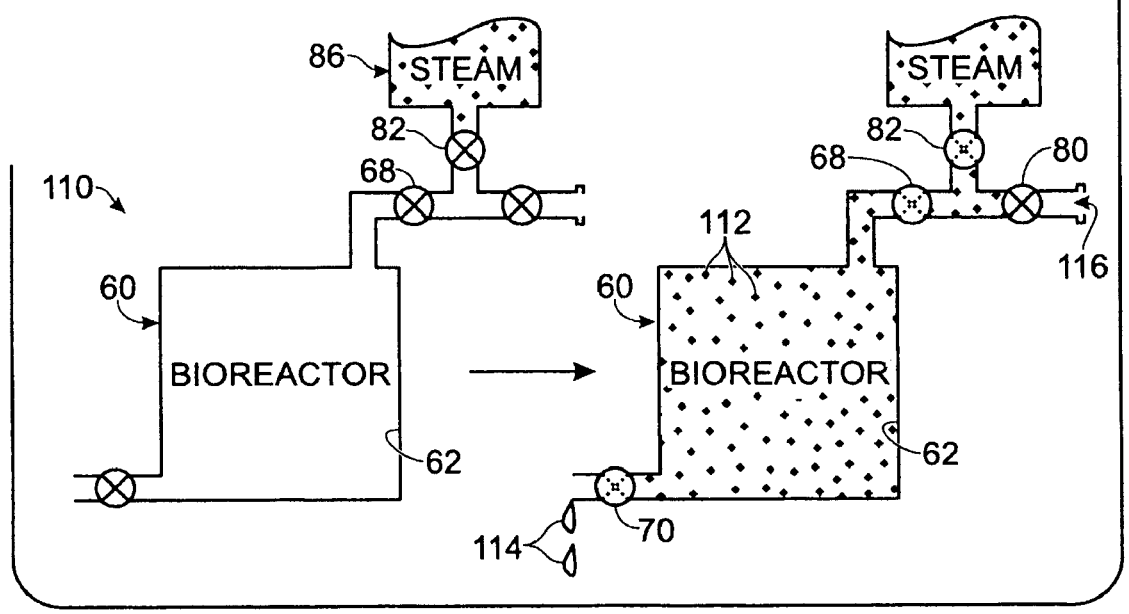
FIG. 2 is a flow diagram illustrating steam-in-place sterilization of a reaction chamber of the bioprocessing system of FIG. 1 before connection of the reaction chamber to the valve, in accordance with aspects of the present teachings.

FIG. 2 shows a flow diagram 110 illustrating steam-in-place sterilization of reaction chamber 62 of bioreactor 60 before connection of the reaction chamber to fluid conduction subsystem 56 and supply vessel 54 (see FIG. 1). On the left, the bioreactor is connected to steam source 86 but is isolated from the steam source by inlet valve 68 and steam valve 82. On the right, valves 68 and 82 are open (indicated by a dashed "X" in each valve) and steam 112 is in reaction chamber 62. Outlet valve 70 also may be open, to function as a drain valve that permits removal of condensate 114 from the reaction chamber. (Generally, steam sterilization may be more effective when condensed steam is removed from the chamber (and/or from a conduit(s)) so that condensate does not shield surfaces from steam contact.) However, here, main channel valve 80 isolates the reaction chamber from a nonsterile port 116 to which the remaining portions of the fluid conduction subsystem will be connected (see below).

Figure 3:
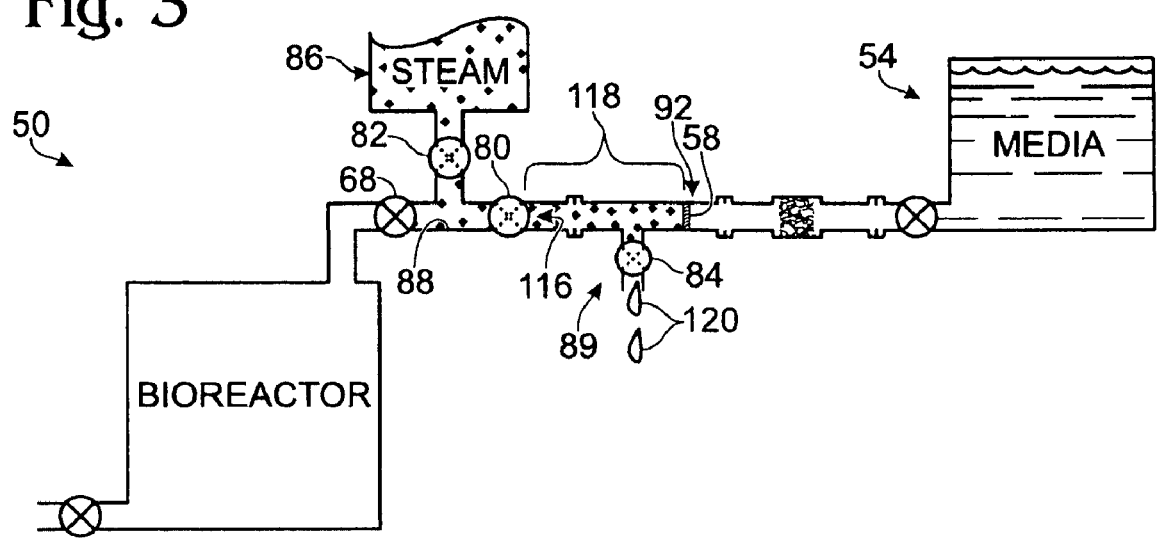
FIG. 3 is a schematic view of the bioprocessing system of FIG. 1, taken during steam-in-place sterilization of an isolated channel disposed between the reaction chamber and the valve, in accordance with aspects of the present teachings.

FIG. 3 shows the steam-sterilized bioreactor of FIG. 2 connected to supply vessel 54 via main channel 88. A channel region 118 defined between channel valve 80 and valve 58 may be nonsterile when conduit assembly 92 is first coupled to port 116. Accordingly, channel region 118 may be sterilized by selective application of steam from steam source 86 to this portion of the main channel. In particular, steam valve 82 and channel valve 80 may be opened to permit steam to pass from the steam source into channel region 118. Inlet valve 68 may open to permit concurrent sterilization of the bioreactor (e.g., if not yet sterile) or may remain closed during this process to keep the bioreactor isolated from the steam (e.g., to keep the sterilization process more efficient and/or to protect steam-sensitive material that may already have been added to the bioreactor). Channel region 118 may be isolated at the other end via valve 58, as described in more detail in the examples of Section V. Steam condensate 120 may be removed during the steam sterilization process using drain 89 by opening drain valve 84.

Figure 4:
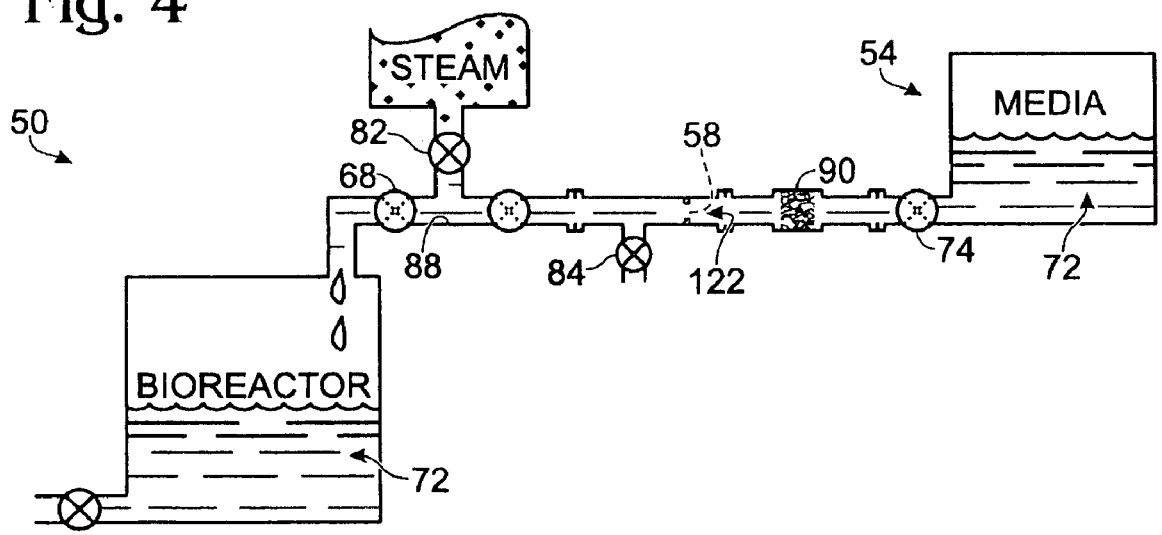
FIG. 4 is a schematic view of the bioprocessing system of FIG. 1, taken after opening of the valve and during addition of a fluid reagent to the reaction chamber through a filter and through a passageway created by valve opening, in accordance with aspects of the present teachings.

FIG. 4 shows bioprocessing system 50 during addition of a fluid reagent from supply vessel 54, after steam sterilization of channel region 118 (see FIG. 3) has been completed. Steam valve 82 has been closed to shut off the steam, and drain valve 84 also has been closed. In contrast, inlet valve 68 of the bioreactor and outlet valve 74 of supply vessel 54 have been opened. Fluid reagent 72 may travel through main channel 88 and through the valve due to opening of the valve, which created a passageway 122 through which the fluid reagent may flow. In FIG. 3, the valve resisted opening when pressure was exerted in an upstream direction (by steam). However, here, the valve has opened in response to pressure exerted in a downstream direction, such as pressure exerted directly or indirectly by fluid reagent 72. The fluid reagent may be filtered as it passes through filter 90, such as to sterilize the fluid reagent, and/or may be added to the bioreactor without filtration (e.g., if the fluid reagent is presterilized or should not be sterilized). Further aspects of using rupture and/or swing valves to regulate fluid flow are described elsewhere in the present teachings, such as in Sections IV and V, among others.

II. CONDUIT ASSEMBLIES

The fluid transfer systems of the present teachings may include one or more conduit assemblies for regulating the flow of fluid within a system. Each conduit assembly may have any suitable structure, particularly a structure selected according to the transfer system for which the conduit assembly is to be used.

The conduit assembly may be packaged in a sterile condition. Accordingly, the conduit assembly may be treated, before or after packaging, with a sterilizing agent that kills microorganisms. The sterilizing agent may, for example, be electromagnetic radiation (e.g., gamma, UV, and/or microwave radiation, among others), heat (e.g., via treatment with steam), a toxic gas (e.g., ethylene oxide), a toxic liquid solution (e.g., formaldehyde and/or hydrogen peroxide), and/or the like. In some examples, exposure of the conduit assembly to radiation may be more suitable because the radiation may be capable of penetrating a sealed package, to allow sterilization of the conduit assembly within the sealed package.

The conduit assembly may have any suitable devices, structures, and features, assembled in any suitable manner, as appropriate. Generally, each conduit assembly has one or more conduits and at least one pressure-responsive valve regulating fluid flow through at least one of the conduits. The conduit assembly also may have one or more additional valves arranged in series or in parallel with the pressure-responsive valve. These additional valves may include a side valve that regulates fluid flow through a side channel and/or an in-line or main valve that regulates fluid flow through a main channel in which the pressure-responsive valve is disposed. In addition, the conduit assembly may include one or more filters (e.g., small-pore filters for removal of microorganisms), one or more chambers or containers for holding fluid, one or more sensors (e.g., any of the sensors described above in Section I), a pump (e.g., powered manually or electrically, among others) to drive fluid through the conduit assembly, and/or the like. Further aspects of conduit assemblies are described elsewhere in the present teachings and below in the following subsections (A) conduits, (B) pressure-responsive valves, and (C) drain valves.

A. Conduits

A conduit assembly may have at least one conduit for channeling fluid through the conduit assembly. The conduit may have any suitable shape and size according to the intended purpose of the conduit assembly.

The conduit (and/or a body tube thereof) may have any suitable shape. For example, for primary flow through the conduit, the conduit may define a main channel that is linear or bent (i.e., curved and/or bent angularly in two or three dimensions). The conduit may be elongate, with a length (measured in the direction(s) of fluid flow) that is substantially greater than the diameter (measured in a direction transverse to fluid flow). Alternatively, in some examples, the conduit's length may be about the same as or less than its diameter. The diameter of the conduit may be substantially uniform or may be nonuniform along the length of the conduit. If nonuniform, the conduit may taper and/or flare generally from inlet end to outlet end, from inlet end to valve, and/or from valve to outlet end, among others. A tapered/flared conduit may be suitable in some cases to provide an end region (e.g., a coupling structure) that is larger or smaller in area than the valve. Alternatively, or in addition, the conduit may widen (or narrow) in an intermediate portion of its length to accommodate an internal device, such as a filter, a sensor, a pump, another valve, and/or the like. The conduit may have any suitable cross-sectional shape, such as circular, oval (with a pair of linear sides), elliptical, polygonal, rosette, and/or the like. In addition, the cross-sectional shape may be substantially the same along the length of the conduit or may be different at two or more positions along the length.

The conduit may be unbranched, to define a single flow path through the conduit, or may be branched, to define alternative flow paths through the conduit. If branched, the conduit may branch any suitable number of times and at any suitable positions in the conduit. For example, the conduit may branch upstream of the valve. An upstream branch may create two or more discrete inlets for the conduit assembly, such as for serial and/or parallel flow of fluid through the valve from two or more fluid sources connected to the conduit assembly. Alternatively, one of the upstream branches may offer an alternative path (e.g., between vessels) that bypasses the valve. Alternatively, or in addition, the conduit may branch downstream of the valve. A downstream branch may create two or more discrete outlets for the conduit assembly, such as for flow of fluid to two or more receiver vessels and/or for alternative flow to either a receiver vessel or to a drain valve. Branched conduits may define branch channels of similar or different sizes. For example, a conduit with an upstream (or downstream) branch may define discrete inlets (or outlets) of about the same cross-sectional area for carrying fluid from different fluid sources (or to different destinations) at about the same flow rate, everything else being equal. In contrast, a conduit with a downstream (or upstream) branch may define discrete outlets (or inlets) of different cross-sectional areas for carrying fluid to different destinations (or from different sources) at different flow rates, everything else being equal.

The conduit may have any suitable size. The length of the conduit generally should be sufficient to allow incorporation of a pressure-responsive valve along the length and, optionally, to a form a coupling structure(s), such as at one or both opposing ends of a body tube of a conduit. However, the length may be extended, as appropriate, to facilitate handling and use, such as a longer conduit to make connections to more widely spaced connection sites. The conduit may have any suitable diameter, generally according to a desired flow rate and/or transfer volume of fluid through the conduit. In particular, the conduit may have a substantially larger diameter and thus a substantially greater flow (and volume transfer) rate than conduits in valves, such as diaphragm valves, used for corresponding fluid transfer applications. For example, in some cases, the conduit may have a diameter of about 0.5 to 10 cm, to accommodate a corresponding range of flow rates and volumes of fluid to be transferred. In some embodiments, the diameter of the conduit may be different after the conduit branches, as described above.

The conduit may have any suitable average wall thickness, generally selected according to the size, composition, and desired strength of the conduit. The wall thickness may be generally uniform or nonuniform along and/or around the conduit. For example, the wall thickness may be thicker adjacent an end(s) of the conduit, to provide a site and/or strength for coupling, and/or may vary to form projections and/or recesses in the outer and/or inner surface(s) of the wall. In some embodiments, the wall may define one or more openings (e.g., through-holes) intermediate the ends of the conduit. The opening(s) may be disposed upstream of the valve, downstream of the valve, or both.

B. Pressure-Responsive Valves

Each conduit assembly may include at least one pressure-responsive valve, such as a rupture and/or swing valve, disposed in a channel defined by a conduit of the conduit assembly. A pressure-responsive valve, as used herein, is any valve that opens in response to pressure exerted on a face of the valve. The pressure-responsive valve may open more selectively in response to pressure exerted on one face of the valve relative to pressure exerted on the other, opposing face of the valve.

A rupture valve, as used here, is any valve that is breached by bursting open, generally irreversibly. Accordingly, the rupture valve may be open permanently after it has ruptured and thus may be a single-use valve suitable for only one use.

The rupture valve may be breached by structural damage to a portion of the valve, generally a rupturable element (an occlusion element) that partially or completely occludes the channel of the conduit assembly. The structural damage may be tearing or breaking of the rupturable element, such as by breaching the element with fluid pressure or with pressure exerted by a solid object, such as a manual actuator, which may be blunt. Alternatively, or in addition, the structural damage may include cutting the rupturable element with a sharp point or sharp edge that engages the rupturable element, such as by breaching the element with a sharp, solid object, such as a manual actuator that is sharp. In some embodiments, the rupture valve thus may be associated with an actuator that engages the actuator to transmit pressure to the rupture valve. The actuator may be capable or producing full rupture of the rupturable element. Alternatively, or in addition, the actuator may be assisted in full rupture of a rupture valve using fluid pressure.

The rupture valve may be breached at a predefined rupture region of the rupture valve. The predefined rupture region may have any suitable shape, size, position, and structure in the rupturable element of the rupture valve.

The shape of the predefined rupture region, as viewed orthogonally to a face of the rupturable element, may be U-shaped, V-shaped, C-shaped, J-shaped, circular, oval, elliptical, polygonal, and/or a combination thereof, among others. The predefined rupture region may define a continuous path or may be comprised of a plurality of discrete segments that are spaced from one another. In addition, the predefined rupture region may extend along and/or around a closed loop(s) or an open loop(s), among others. Furthermore, the predefined rupture region may be shaped to maximize the flow rate through the rupture valve after rupture. Accordingly, the predefined rupture region may be designed as a compromise between the size of opening produced by rupture and the angle of flexion permitted by the size/shape of the predefined rupture region in conjunction with its proximity to conduit walls.

The predefined rupture region may have any suitable size and position in relation to a corresponding rupturable element and/or conduit. For example, the predefined rupture region may define a shape with a diameter that is slightly less than or substantially less than the diameter of the rupturable element. In addition, the diameter of the predefined rupture region may be about the same as (although generally slightly less than) the inner diameter of a corresponding conduit, such that the predefined rupture region is disposed near to the inner surface of the conduit. However, in some examples, the predefined rupture region may be spaced (radially inward) from the inner surface of the conduit, so that the predefined rupture region can be supported by a support element and/or seating structure of the rupture valve that extends radially inward from the conduit inner surface (e.g., see Examples 1 and 2). The predefined rupture region may have any suitable depth relative to the thickness of a corresponding rupturable element. For example, the predefined rupture region may be less than, at least about one-half, or substantially greater than one-half the thickness. In some embodiments, the predefined rupture region may be a structurally weakened portion of the rupturable element that is created without reducing the thickness of the rupturable element. For example, the rupturable element may be weakened locally via treatment with light (e.g., a laser), heat, pressure (e.g., bending), and/or the like. The predefined rupture region may occupy any suitable portion of the area of a rupturable element, although generally substantially less than one half.

The rupture valve (and/or a swing valve) may be configured to have any suitable resistance to pressure exerted on the rupture valve in a first (e.g., upstream) direction in the conduit and any suitable sensitivity to pressure exerted on the rupture valve (and/or swing valve) in a second, opposing (e.g., downstream) direction in the conduit. Generally, the rupture valve (and/or swing valve) may be capable of resisting opening of the valve in response to pressure, exerted in the first direction, that is substantially greater than atmospheric pressure, for example, at least about 50% more than, or at least about twice or three times atmospheric pressure. In addition, the rupture valve (and/or swing valve) may be configured to resist opening in response to a relatively small pressure exerted in the second direction, which may avoid inadvertent opening of the rupture valve due premature pressure fluctuations prior to deliberate opening of the valve. Furthermore, the rupture valve (and/or swing valve) may be configured to open in response to any suitable increased pressure on the valve. The rupture characteristics of the rupture valve may be selected based on the material and thickness of the rupturable element, the size and shape of the predefined rupture region in the rupturable element, the position of the predefined rupture region, the position of a support element relative to the rupturable element/predefined rupture region, and/or the inner diameter of the conduit, among others.

The rupture valve (and/or a swing valve) may have any suitable longitudinal and angular disposition in a conduit assembly. For example, the rupture valve (and/or swing valve) may be disposed generally centrally along the length of a conduit of the assembly. Alternatively, or in addition (such as with an assembly including a plurality of rupture valves), the rupture valve (and/or swing valve) may be disposed near an end of the conduit. In addition, the rupture valve (and/or a swing valve) may be disposed orthogonally in the conduit (e.g., defining a plane that is orthogonal to a primary flow axis of the conduit) (e.g., see Example 3) or may be disposed obliquely (e.g., see Examples 1, 2, and 4-8).

A swing valve may be any valve operatively coupled to a conduit to regulate fluid flow therethrough and incorporating an occlusion element, wherein at least a portion of the occlusion element swings with respect to the conduit when the swing valve changes from a closed configuration to an open configuration. The occlusion element may be a discrete piece, such as a pivotable disc, or may be a rupturable element, among others. The swing valve may be a single-use valve or may be opened and then closed again.

C. Drains

A conduit assembly may have one or more drains (also termed ports or vents) for removing fluid laterally from a conduit of the conduit assembly. Each drain may include a drain conduit (which may be a lateral opening in a conduit) and, optionally, one or more valves (termed drain valves or bleed valves) for regulating fluid movement through the drain conduit. The one or more valves may be arranged in parallel or in series relative to one another.

A drain valve may have any suitable structure and mechanism of operation. Accordingly, the drain valve may, for example, be an angle, ball, butterfly, diaphragm, flapper, gate, globe, needle, pinch, slide, stopcock, and/or thumbscrew valve, among others. The drain valve may be driven and/or controlled (e.g., opened, closed, or adjusted at selected times) manually and/or according to a threshold or change in temperature, pressure, presence/absence of fluid, and/or the like. The temperature, pressure, presence/absence of fluid, etc. may be sensed mechanically or electronically, among others. In some embodiments, a drain valve may function as a check valve (such as in a steam trap) that opens selectively to release liquid water and closes to retain steam.

The drain valve may control flow through a drain channel of any suitable size. The drain channel may have about the same cross-sectional area as a main channel of the conduit assembly or may be substantially smaller in cross-sectional area.

III. METHODS OF MAKING CONDUIT ASSEMBLIES

The conduit assemblies of the present teachings may be fabricated by any suitable methods. The methods may use any suitable number of components, components of any suitable composition(s), and components connected to one another by any suitable connection mechanism(s).

A conduit assembly may be assembled from any suitable number of components. For example, the conduit assembly may be assembled using a discrete component(s) that forms or contributes to a valve (e.g., a rupturable element and/or a disc thereof) and one or more other discrete components that form the conduit (e.g., see Examples 2-8). Alternatively, or in addition, the conduit assembly may have at least part of the conduit and part of the valve formed by the same component (e.g., see Example 1).

A conduit assembly may have any suitable composition. Generally, however, the conduit assembly (or at least an outlet thereof) may have a composition that is capable of withstanding exposure to steam without substantial warping or melting.

In exemplary embodiments, at least a portion of the conduit assembly may be constructed of plastic, particularly steam-resistant plastic. The components of a conduit assembly may be formed of the same material or of different materials. For example, the conduit may be formed of a harder, stronger plastic; a support element of a rupture valve also may be formed of a harder, stronger plastic; and a rupturable element of the rupture valve may be formed of a softer, weaker plastic. In some examples, at least a portion of the conduit may be formed of a more flexible material, such that the conduit assembly may be bendable to facilitate connection of the conduit assembly to upstream and/or downstream connection sites.

The components of a conduit assembly may be connected to one another by any suitable mechanism(s). Exemplary mechanisms may include an adhesive, welding, bonding, an interference fit, a fastener(s), and/or the like.

IV. METHODS OF USING CONDUIT ASSEMBLIES

The conduit assemblies of the present teachings may be used in any suitable fluid transfer operations for any suitable purpose. An exemplary method of using a conduit assembly including a pressure-responsive valve, such as a rupture valve and/or a swing valve, is presented here. The method steps listed may be performed in any suitable order, in any suitable combination, and any suitable number of times.

A conduit assembly may be selected. The conduit assembly may include any combination of the components, structures, and/or features described in the present teachings. The conduit assembly may include a conduit and a valve. The conduit may define a channel, and the valve may block fluid flow through the conduit to divide the channel into a first/inlet portion (an upstream portion) and a second/outlet portion (a downstream portion). The valve may be opened selectively in response to pressure exerted in a downstream direction on the valve. The conduit assembly may be sterilized by any of the treatments described elsewhere in the present teachings. Sterilization of the conduit assembly may be performed before (and/or after) the conduit assembly is connected to a downstream receiver, such as a conduit and/or process vessel. Furthermore, sterilization of the conduit assembly may be performed after (and/or before) the conduit assembly is connected to an upstream device, conduit, and/or vessel.

A sterilizing agent may be applied to the second/outlet portion of the conduit assembly, for example, after the conduit assembly has been connected to a downstream receiver, such as a downstream conduit and/or process vessel. The sterilizing agent may be any of the agents described herein, for example, steam. The valve may restrict entry of the sterilizing agent into the first/inlet portion of the conduit assembly by resisting rupture during application of the sterilizing agent. If steam is used as the sterilizing agent, the steam may have a suitable temperature and pressure for killing microorganisms. In addition, application of the steam (or other sterilizing agent) may be performed over a time period (in conjunction with the steam temperature and pressure) that is sufficient, to "sterilize" the second/outlet portion of the conduit assembly. The terms "sterilize" and "sterilization," as used herein, refer to a process or procedure that results in, or would be expected to result in, a substantial reduction in microorganism viability. The substantial reduction may be described as a "log kill" of any suitable magnitude, such as a one-log kill (i.e., a tenfold reduction in viability), a two-log kill, a three-log kill, a six-log kill, and/or the like. Similarly, the term "sterile" is intended to mean a condition of substantially reduced microorganism viability produced by sterilizing or sterilization.

A drain valve of the conduit assembly (or another valve spaced from the conduit assembly but in fluid communication therewith) may be opened before and/or during application of the sterilizing agent. Opening of the drain valve may be performed manually or automatically. Furthermore, the drain valve may be opened only once, before or during application of the sterilizing agent, or may be opened repeatedly.

The pressure-responsive valve may be opened after the step of applying, with pressure exerted in a downstream direction from the first/inlet portion. The pressure may be exerted by upstream fluid. For example, pressure may be exerted directly by a fluid reagent from an upstream fluid source. Alternatively, the pressure may be exerted indirectly by the fluid reagent, such as via gas that is disposed downstream of the fluid reagent in the inlet portion. In some embodiments, the pressure may be exerted manually via an actuator coupled to a valve face that adjoins the first/inlet portion.

Any suitable fluid reagent(s) may flow through the open valve for transfer of the fluid reagent to a downstream site. The fluid reagent may be substantially liquid, such as water, an aqueous solution/mixture, a buffer, a suspension of particles (e.g., cells) in a liquid, a growth medium, a non-aqueous liquid or mixture, any combination thereof, or the like. Alternatively, or in addition, the fluid reagent may be substantially gas, a gas mixture, and/or the like. In addition, any suitable volume of the fluid reagent may flow through the valve, such as at least about one or 100 L, among others. In some embodiments, the volume may be at least about 1,000 L, or may be up to about 100,000 L, or more.

The fluid reagent may flow to any suitable destination. Exemplary destinations may include a discrete downstream conduit, a vessel, a chamber (such as a bioreactor chamber), a vial, a microplate, any combination thereof, etc. The destination may be in a sterile condition (at least interiorly) or may be nonsterile.

The opened valve may be used for fluid transfer from and to any suitable number of fluid sources and fluid destinations. Two or more fluid transfers may be performed in series, such as by serially connecting different fluid sources and/or different receiver vessels to the same conduit assembly. Alternatively, or in addition, two or more fluid transfers may be performed in parallel, such as by using a conduit assembly with a branched conduit structure that allows concurrent connection to two or more fluid sources and/or two or more receiver vessels.

V. EXAMPLES

The following examples describe selected aspects and embodiments of the present teachings, particularly exemplary conduit assemblies and methods of using the conduit assemblies to regulate fluid flow and/or transfer fluid. These examples and the various features and aspects thereof are included for illustration and are not intended to define or limit the entire scope of the present teachings.

Example 1

Conduit Assembly with Oblique Rupture Valve

This example describes an exemplary conduit assembly 140 including a conduit and a rupture valve with an oblique disposition within the conduit; see FIGS. 5-11.

Figure 5:
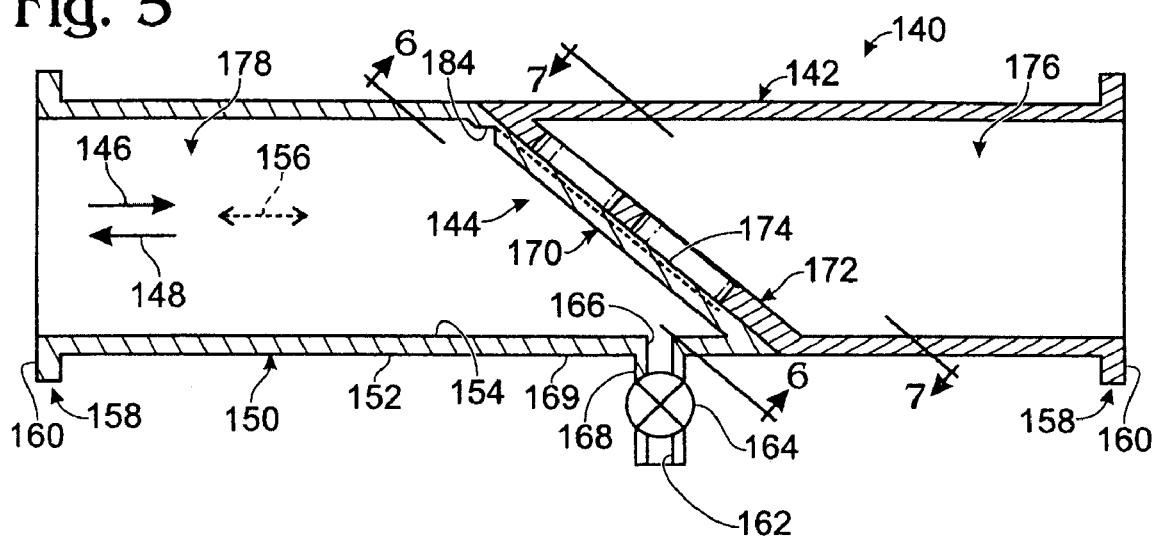
FIG. 5 is a longitudinal sectional view of an exemplary conduit assembly including a rupture valve disposed obliquely in a conduit of the assembly, in accordance with aspects of the present teachings.

FIG. 5 shows a longitudinal sectional view of conduit assembly 140. The conduit assembly may include a conduit 142 and a rupture valve 144 that regulates fluid flow through the conduit.

Conduit 142 may be structured to define opposing directions of (potential) flow, namely, upstream direction 146 and downstream direction 148. The conduit thus may have a body or body tube 150 having an outer wall 152 defining a main or longitudinal channel 154, which may extend parallel to a long axis 156 of the conduit. The body tube may be a hollow cylinder or may have any other suitable shape (see Section II above).

The conduit also may have any other suitable structures. For example, the conduit may have opposing end regions 158 that provide coupling structures, such as flanges 160, for making sealed connections to other conduits and/or vessels. The flanges may extend radially outward of wall 152 of the body tube in a circumferential arrangement to provide structure suitable for engagement with a clamp (such as a tri-clamp fitting to be secured by a tri-clamp). The conduit also may define a side or ancillary channel 162 connected to a side or drain valve 164 to create a drain. Accordingly, the body tube of the conduit may define an opening 166 in wall 152 that communicates with the drain. Furthermore, ancillary channel 162 may be defined by an ancillary conduit 168 that projects laterally from a main conduit 169, such that conduit 142 is branched.

Rupture valve 144 may be structured asymmetrically for differential sensitivity to pressure exerted in the opposing directions of flow 146, 148. In particular, the rupture valve may have a rupturable element (an occlusion element) 170 that occludes main channel 154, and a support element (e.g., a backing plate) 172 disposed adjacent the rupturable element, for example, adjacent an upstream face 174 of the rupturable element. The rupture valve thus may divide main channel 154 into an inlet portion 176 and an outlet portion 178, and the support element may be adjacent the inlet portion.

The rupturable element (and, optionally, the perimeter of the support element) may extend circumferentially to outer wall 152 of the conduit, to provide a sealed relationship with the outer wall that blocks fluid flow through the conduit. Accordingly, the rupturable element may be structured as a disc. Here, the rupturable element (and the rupture valve and the support element) has an oblique orientation relative to the conduit, that is, the rupturable element defines a plane disposed obliquely relative to the conduit and/or relative to a long axis thereof.

Conduit assembly 140 may have any suitable number of pieces formed and connected by any suitable approach. In some examples, the conduit assembly may have rupture valve 144 and body tube 150 formed by only two components, namely, an upstream component and a downstream component, as shown here. Ancillary conduit 168 may be unitary with the downstream component or may be a separate component that is attached to the downstream component. Similarly, flanges 160 may be unitary with their respective upstream and downstream components or may be formed separately and attached to the components.

Figure 6:
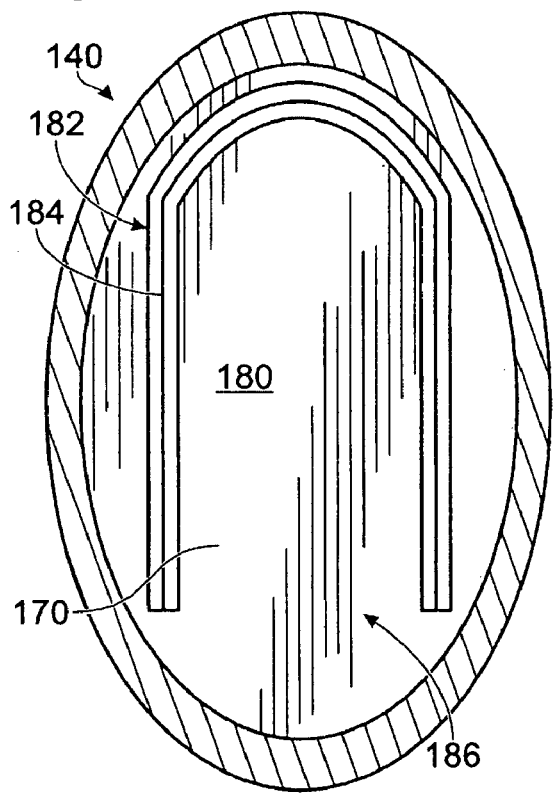
FIG. 6 is a cross-sectional view of the conduit assembly of FIG. 5, taken generally along line 6-6 of FIG. 5 from an outlet (downstream) side of the rupture valve.

FIG. 6 shows a cross-sectional view of conduit assembly 140 taken from outlet portion 178 (see FIG. 5), toward a downstream face 180 of rupturable element 170. The rupturable element may be structured such that a predefined region 182 of the rupturable element tears and/or fractures when the rupturable element ruptures. The predefined region may be structurally weaker than other portions of the rupturable element. For example, the rupturable element may be fabricated and/or pre-cut (e.g., scored) to form a groove or slit in one or both opposing faces of the rupturable element. Here, the downstream face of the rupturable element has a generally U-shaped groove 184 extending adjacent a majority of the perimeter of the rupturable element (see FIG. 5 also). The groove (or other structurally weakened region) may extend in a closed loop or may extend in an open loop configuration, as shown here, among others. In any case, the groove (or other weakened region) may terminate or may be shallower (and/or less weak) along a portion of a circumferential path to form a hinge region 186 at which the rupturable element may flex without tearing/fracturing. This structural arrangement may provide a rupturable element that ruptures efficiently and flexes (e.g., pivots) to move out of the flow path (i.e., dispose its opposing faces generally parallel to the flow path), without detaching completely from the conduit assembly.

Figure 7:
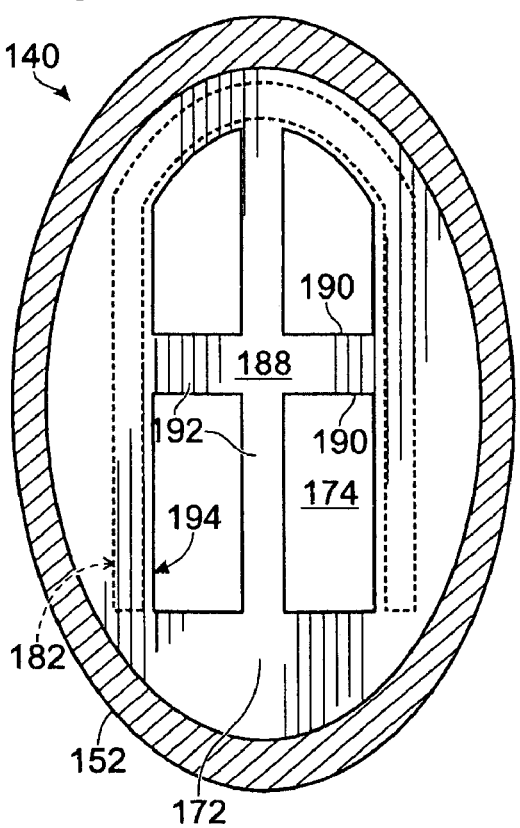
FIG. 7 is a cross-sectional view of the conduit assembly of FIG. 5, taken generally along line 7-7 of FIG. 5 from an inlet (upstream) side of the rupture valve.

FIG. 7 shows a cross-sectional view of conduit assembly 140 taken from inlet portion 176 (see FIG. 5), toward an upstream face 188 of support element 172 (and toward upstream face 174 of rupturable element 170). Support element 172 may define one or more openings 190 for fluid flow through the conduit after rupture of the rupturable element. For example, the support element may define a plurality of openings separated by brace elements 192 that support the rupturable element centrally. The support element also or alternatively may support the rupturable element laterally, for example, extending inward, indicated at 194, from outer wall 152 of the conduit to overlap and/or extend beyond and support predefined rupture region 182.

FIG. 8 shows conduit assembly 140 during application of steam 210 to outlet portion 178. The steam is exerting a pressure, indicated by an open arrow at 212, on rupture valve 144, via contact with downstream face 180 of rupturable element 170. The term "pressure," as used herein, means a net positive pressure. Accordingly, here, the steam creates a pressure drop directed upstream in the conduit assembly through the rupture valve. In this configuration, the rupturable element resists rupture because the support element restricts upstream movement of the rupturable element that otherwise may promote tearing/fracture at the predefined rupture region of the rupturable element (see FIG. 6).

FIG. 9 shows conduit assembly 140 after rupture of rupture valve 144. A pressure, indicated by an open arrow at 214, exerted on upstream face 174 of rupturable element 170 from inlet portion 176 of the conduit assembly, may cause the rupturable element to fail. In particular, the rupturable element may burst because the support element is not providing support against pressure exerted on the upstream face of the rupturable element. Rupture of the rupturable element may create a passageway 216 through which fluid 218 may flow toward outlet portion 178 of the conduit assembly. Rupture of the rupturable element also may cause the rupturable element to pivot via hinge region 186 such that the rupturable element moves out of the flow path for approximate alignment with the direction of fluid flow.

FIGS. 10 and 11 show conduit assembly 140 in respective horizontal and vertical orientations of conduit 142 during application of steam 210. The oblique arrangement of the rupture valve may direct condensate 230 toward a drain 232 in each orientation of the conduit. In particular, condensate 230 may be urged by gravity along downstream face 180 of rupturable element 170 due to its oblique disposition, whether or not face 180 is facing generally downward (FIG. 10) or generally upward (FIG. 11). A rupture valve with an oblique orientation within a conduit assembly thus may provide greater flexibility in how the conduit assembly is oriented during its use.

Example 2

Conduit Assembly with Orthogonal Rupture Valve

This example describes an exemplary conduit assembly including a conduit and a rupture valve with an orthogonal disposition within the conduit; see FIG. 12.

FIG. 12 shows another exemplary conduit assembly 250 viewed before (top) and after (bottom) rupture of a rupture valve 252 of the conduit assembly. The top panel of FIG. 12 shows conduit assembly 250 during steam sterilization of an outlet portion 254 of the assembly. The bottom panel of FIG. 12 shows the conduit assembly conducting fluid 256 through a passageway 258 created by valve rupture.

Rupture valve 252 may be arranged orthogonally relative to a conduit 260 of the conduit assembly. In particular, a rupturable element (an occlusion element) 262 and a support element 264 of the rupture valve each may define planes that are orthogonal to a flow direction through conduit 260 (and/or a long axis defined by the conduit).

The rupturable and support elements may be connected to conduit 260 by components that are separate from the conduit. For example, conduit 260 may include an upstream conduit component 266 and a downstream conduit component 268 that are attached to rupturable element 262 and support element 264 components via polymer welds 270, 272.

Example 3

Conduit Assembly with Face-to-Face Valve Elements

This example describes an exemplary conduit assembly 290 including a rupture valve 292 having a rupturable element 294 and a support element 296 disposed in a face-to-face relationship; see FIGS. 13 and 14.

Rupture valve 292 may have rupturable element 294 and support element 296 structured as separate components that are attached to one another, face-to-face, within a conduit 298 of the conduit assembly. The rupturable element may be a sheet of material and/or a disc that has been scored, indicated at 300, with a cut extending partway through the sheet/disc, to define a region at which the rupturable element will tear/fracture during rupture. The cut may extend adjacent the perimeter of the sheet/disc, partway (or completely) around the perimeter. The rupturable element and the support element may be held in position by the conduit. In particular, the conduit may have upstream and downstream conduit components 302, 304 that form a circumferential seal near the perimeter of the rupturable element, on respective opposing faces thereof. Furthermore, upstream conduit component 302 may project inward into the conduit channel to create a buttress structure 306 (also termed a seating structure) with recesses 308 for receiving and engaging the support element, as indicated at 310, and thus restricting its upstream movement. The buttress structure also may engage and support a perimeter region of the rupturable element, indicated at 312.

FIG. 13 shows conduit assembly 290 during steam sterilization. Here, rupture valve 292 is intact, with support element 296 seated against buttress structure 306.

FIG. 14 shows conduit assembly 290 after rupture valve 292 has ruptured. Here, rupturable element 294 has been torn, and both the rupturable element and the support element have pivoted together, indicated at 314, to form a passageway 316 for fluid flow through the conduit.

Example 4

Conduit Assembly with Pinch Valve

Figure 15:
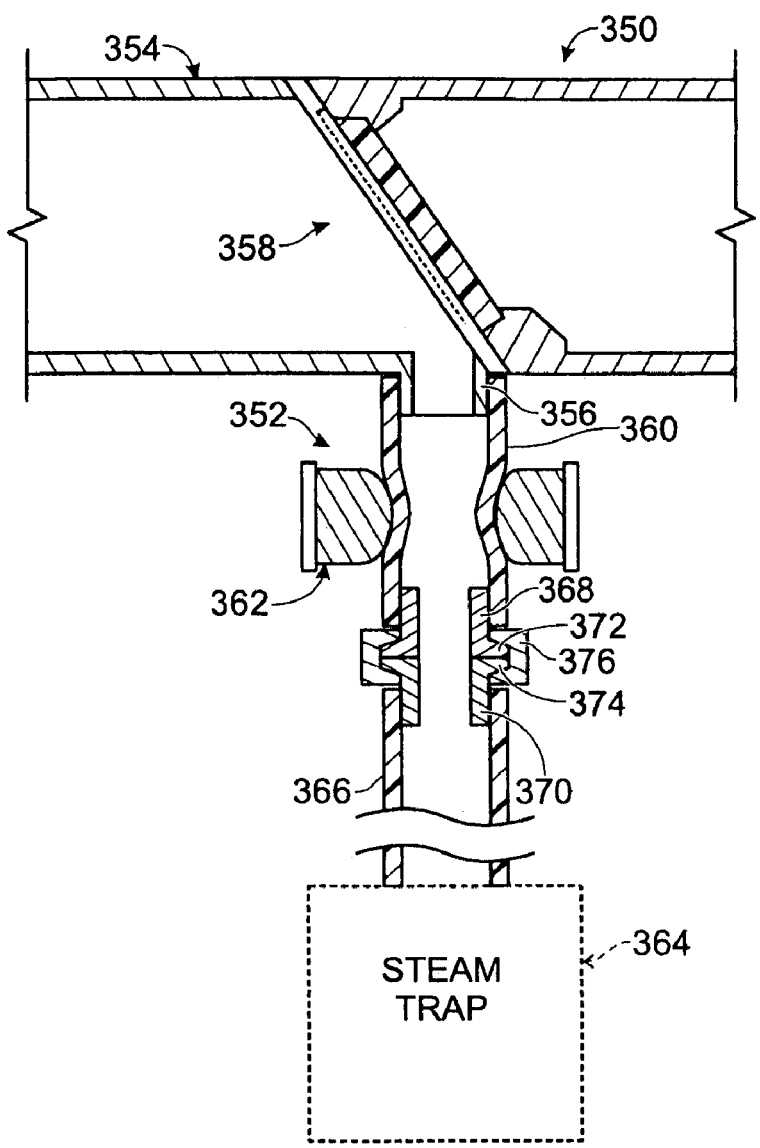
FIG. 15 is a fragmentary, longitudinal sectional view of an exemplary conduit assembly having a drain valve structured as a pinch valve created by flexible tubing and a clamp, and connected to a steam trap, in accordance with aspects of the present teachings.

This example describes an exemplary conduit assembly 350 including a drain valve 352 structured as a pinch valve; see FIG. 15.

Conduit assembly 350 include have a primary conduit 354 and an ancillary conduit 356 that branches laterally from the primary conduit. Flow through the primary conduit may be regulated by a rupture valve 358, which here is structured similarly to rupture valve 292 of Example 3.

The ancillary conduit may be configured to be received in a piece of flexible tubing 360. For example, the ancillary conduit may be a hollow tube with a nonflanged end (or a flanged end (see Example 5) or a ribbed/barbed shank, among others). The ancillary conduit may be formed unitarily with a portion of the primary conduit or may be formed separately and attached to the primary conduit after formation. Fluid flow through the ancillary conduit (and through the flexible tubing) may be controlled by a clamp 362 positioned to compress the flexible tubing, thereby forming pinch valve 352.

In some examples, the conduit assembly may be connected to a steam trap 364. The steam trap may be configured to open at appropriate times, for example, when condensate is present, and to close otherwise, to reduce unnecessary loss of steam pressure and temperature. Here, the steam trap is connected to flexible tubing 360 by additional tubing 366 via connector pipes 368, 370 having paired tri-clamp fittings 372, 374 secured with a tri-clamp 376.

Example 5

Conduit Assembly with Ancillary Conduit

Figure 16:
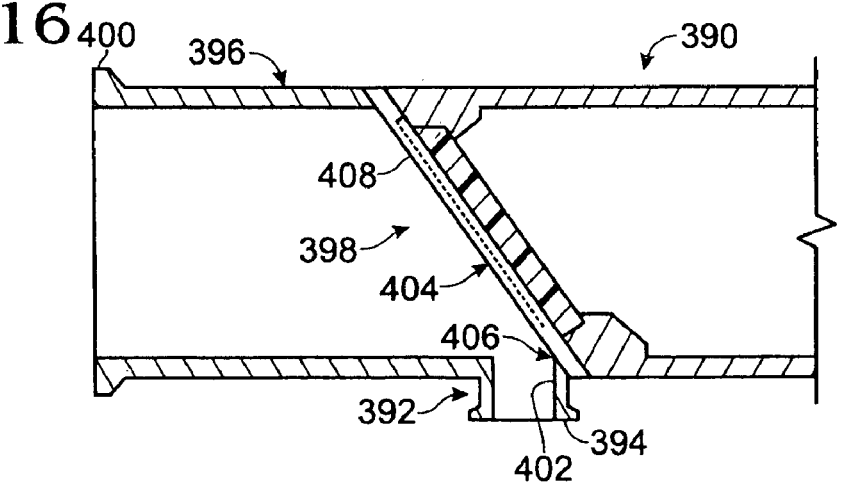
FIG. 16 is a fragmentary, longitudinal sectional view of an exemplary conduit assembly having an ancillary (drain) conduit with a tri-clamp fitting, in accordance with aspects of the present teachings.

This example describes an exemplary conduit assembly 390 having an ancillary conduit 392 with a tri-clamp fitting 394; see FIG. 16.

Conduit assembly 390 may include a main conduit 396 and a rupture valve 398 occluding the main conduit. The main conduit may have a tri-clamp fitting 400 at one or both opposing ends of the conduit. The rupture valve may be structured generally as described above in Example 3.

Ancillary conduit 392 may be positioned to receive condensate at least relatively directly from rupture valve 398. For example, the ancillary conduit made define a passage or through-hole 402 with a longitudinal location along the main conduit that overlaps the longitudinal position of the rupture valve. More particularly, a rupturable element 404 of the rupture valve may extend along a range of longitudinal positions of the main conduit, and passage 402 may be disposed adjacent an upstream/inlet end of the range of longitudinal positions. In some examples, passage 402 may at least substantially adjoin the rupturable element, indicated at 406, such that condensate may flow at least substantially directly from a downstream face 408 of the rupturable element to the passage.

Example 6

Conduit Assembly with Swing Valve

This example describes an exemplary conduit assembly 420 including a swing valve 422 that utilizes a discrete, pivotable disc 424 for controlling fluid flow; see FIGS. 17-19.

FIG. 17 shows a fragmentary, longitudinal sectional view of conduit assembly 420 during steam-in-place sterilization by application of steam 426, which applies a steam pressure indicated at 428. In the present illustration, swing valve 422 is in a closed configuration that blocks fluid flow through the swing valve and conduit assembly.

Conduit assembly 420 may include at least one conduit 430 defining a channel 432. The channel may be linear, bent angularly, curved, or any combination thereof, among others. The conduit assembly also may define at least one lateral port 434 defining an opening 436 in a wall 438 of conduit 430. Port 434 may be disposed on a downstream side of swing valve 422, as shown here, which may permit removal of steam condensate through the port. Alternatively, or in addition, a port may be disposed on an upstream side of swing valve 422 (e.g., see Example 8).

Swing valve 422 may divide channel 432 into channel portions 440, 442 (e.g., downstream and upstream channel portions, respectively, or vice versa). In the closed configuration of swing valve 422 shown in FIG. 17, channel portions 440, 442 are in fluid isolation from one another.

Disc 424 may have any suitable structure. For example, disc 424 may include opposing faces 444, 446 connected by side surfaces 448. The side surfaces may define a perimeter of the disc. The disc may have any suitable shape. For example, the disc or at least a body thereof may be generally planar, with each of faces 444, 446 being at least substantially planar. In addition, side surfaces 448 may be arranged to form a disk that is circular, elliptical, at least generally polygonal (with or without rounded corners), or the like.

Disc 424 of the swing valve may be disposed in a sealed connection with conduit 430, to create a seal 450 between the disc and the conduit. The term "sealed connection," as used herein, means that an at least substantially fluid-tight seal is formed and flow of fluid is blocked. In other words, swing valve 422 may hermetically seal conduit 430 against flow of fluid through the conduit. The sealed connection may be formed, at least in part, by disc 424 received in a seating structure 452 (also termed a buttress structure) of conduit 430. The seating structure may be formed integrally with walls 438 of the conduit and may project inwardly therefrom, as shown here, or may be formed by one or more discrete pieces secured to the inner surface of the walls.

A sealed connection may be formed by contact of the disc and the seating structure. Alternatively, in some embodiments, the sealed connection may be formed, at least in part, by a sealing member, such as a gasket 454 (e.g., an O-ring) disposed between the disc and the seating structure, and in fluid-tight engagement with both the disc and the seating structure. Gasket 454 (or another sealing member) may contact side surfaces 448 (as shown here), upstream face 446, or both, among others. The gasket (or sealing member) may be formed of any suitable material. For example, the gasket may be formed an elastic material, which may be more flexible and/or compressible than the material forming the disc and/or the seating structure. The gasket may be attached to the disc or the seating structure. For example, in the present illustration, gasket 454 is received and retained in an annular recess 456 defined by side surfaces 448 of the disc. Gasket 454 may be held in place on the disc or seating structure by gasket tension or may be secured to the disc or the seating structure by any other suitable attachment mechanism, such as with an adhesive, by bonding, and/or the like.

Disc 424 also may be coupled to conduit 430 movably by a movable joint 458, which may permit translational and/or pivotal motion of the disc with respect to the conduit. The movable join may, for example, be formed by a pin 460 received in an aperture 462 defined by a flange 464 projecting from a body 466 of disc 424. Aperture 462 may be elongate in a direction transverse to a plane defined by body 466 and/or in a direction transverse to a central axis 468 defined by pin 460. The aperture thus may be described as a slot, which permits translational motion of the disc in a direction transverse (or at least substantially orthogonal) to the plane defined by the body of the disc. In any event, the aperture permits pivotal motion of the disc about central axis 468 of pin 460.

Seating structure 452 may be configured to support disc 424 selectively adjacent upstream face 446 relative to downstream face 444. For example, the seating structure may be disposed adjacent and/or may be in contact with upstream face 446. Accordingly, net pressure, such as steam pressure 428, exerted on downstream face 444 of disc 424 urges the disc toward and/or against the seating structure, thereby maintaining swing valve 422 in the closed configuration.

FIG. 18 shows a fragmentary, longitudinal sectional view of conduit assembly 420 with swing valve 422 in an open configuration. In the open configuration, a fluid reagent 470 (and/or a liquid) may flow, indicated at 472, through the swing valve and through conduit 430 from upstream channel portion 442 to downstream channel portion 440. Alternatively, or in addition, the fluid reagent and/or liquid may flow in the opposing direction from channel portion 440 to channel portion 442.

Swing valve 422 may be placed in the open configuration by net pressure exerted on upstream face 446 of disc 424. The net pressure may be exerted by contact of fluid reagent 470 with the disc, or by pressure exerted by fluid reagent 470 on air (or another gas) that is disposed in contact with disc 424. In any event, the net pressure may push disc 424 out of its seated position and may pivot the disc, to create a passageway through the swing valve for fluid flow.

FIG. 19 shows a sectional view of conduit assembly 420, taken generally along line 19-19 of FIG. 17. Pin 460 may extend to generally opposing walls 438 of conduit 430. The pin may be received in sockets 474 formed in walls 438, may be attached by any other suitable mechanism to the walls, or may be formed integrally with the walls.

Example 7

Conduit Assembly with Manually Actuated Valve

Figure 20:
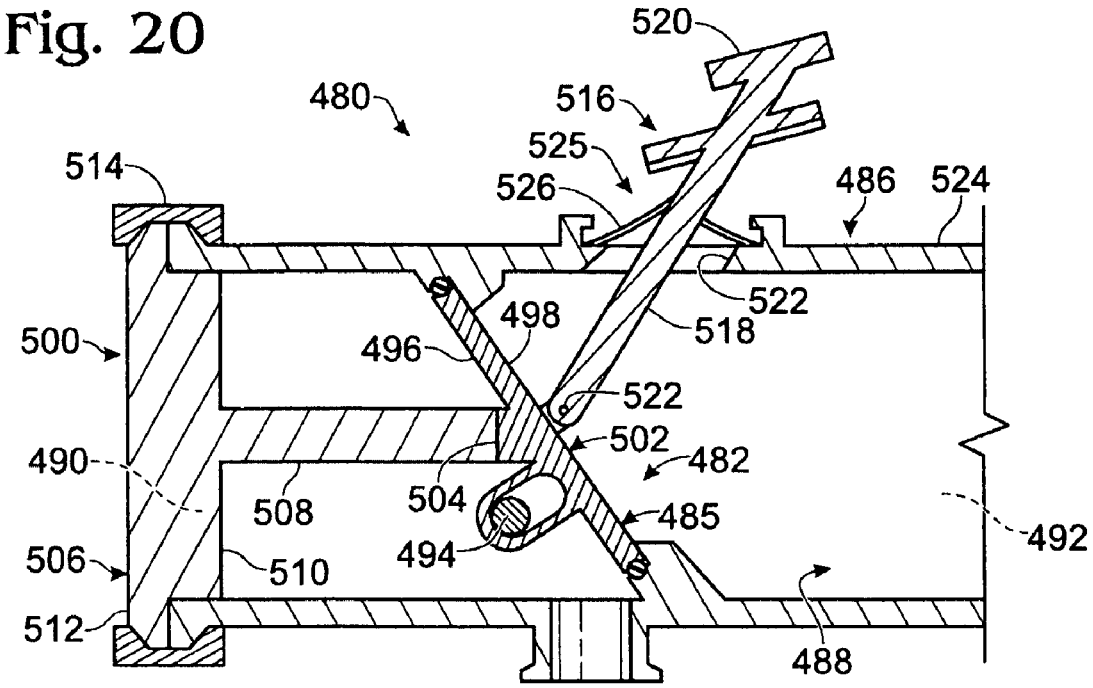
FIG. 20 is a fragmentary, longitudinal sectional view of an exemplary conduit assembly including a manually actuated valve for use in steam sterilization, with the manually actuated valve locked in a closed configuration by a detent member, in accordance with aspects of the present teachings.
Figure 21:
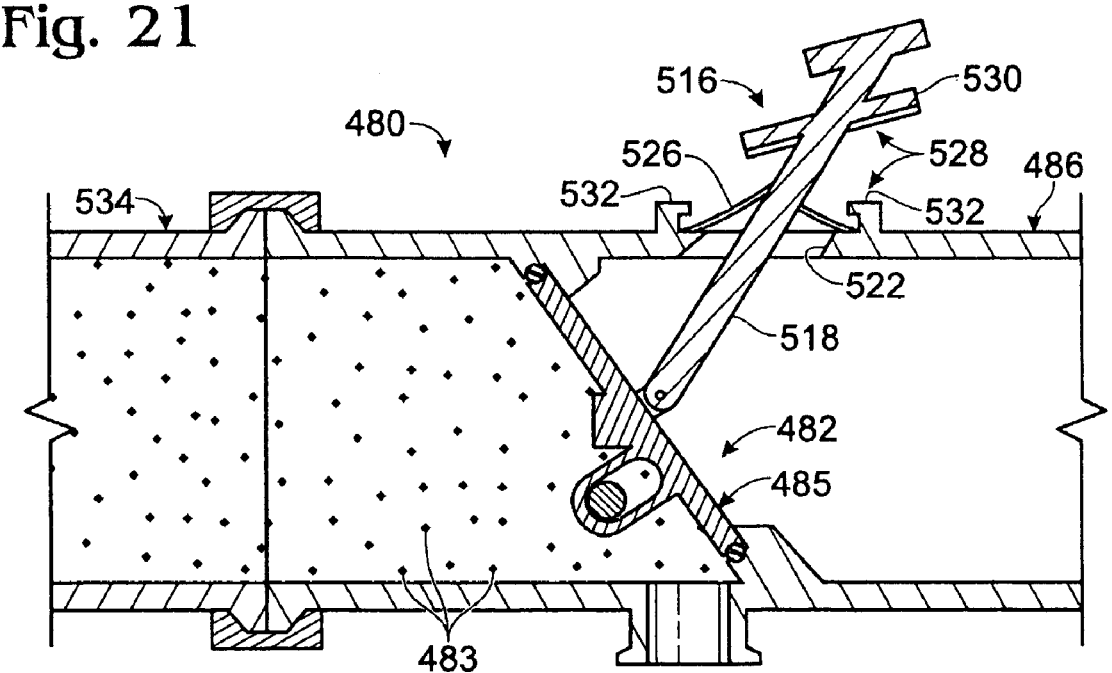
FIG. 21 is a fragmentary, longitudinal sectional view of the conduit assembly of FIG. 20 being used in steam sterilization, with the manually actuated valve still in the closed configuration but with the detent member removed to unlock the valve, in accordance with aspects of the present teachings.
Figure 22:
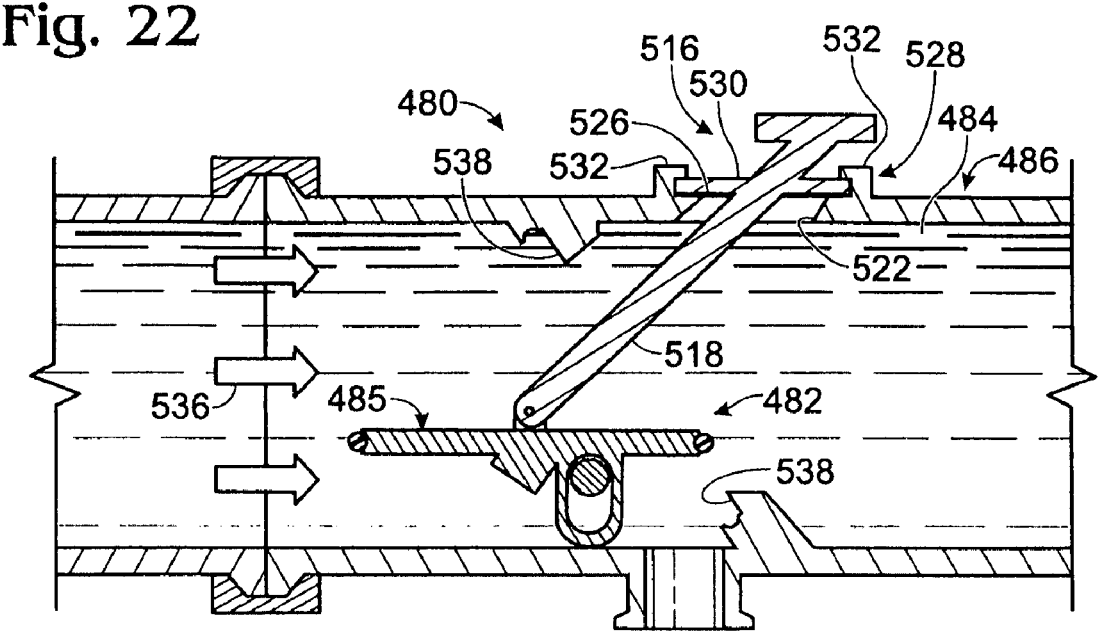
FIG. 22 is a fragmentary, longitudinal sectional view of the conduit assembly of FIG. 20 after the valve has been opened manually and locked in an open configuration and with fluid flowing through the open valve.

This example describes an exemplary conduit assembly 480 including a valve 482 that is configured to be actuated manually and, optionally, by fluid pressure; see FIGS. 20-22.

FIGS. 20-22 show fragmentary, longitudinal sectional views of conduit assembly 480 with valve 482 locked in a closed configuration (FIG. 20), valve 482 unlocked during application of steam 483 (FIG. 21), and after opening valve 482 manually (FIG. 22) with a fluid reagent 484 flowing through the valve. Valve 482 may be a rupture valve and/or a swing valve. Here, valve 482 is a swing valve with a discrete disc 485 that pivots to open the valve. In other embodiments, the valve may include an occlusion element (e.g., a disc) that ruptures to open the valve.

Conduit assembly 480 may include a conduit 486 defining a channel 488 having opposing ends 490, 492 (see FIG. 20). Disc 485 may be pivotably coupled to conduit 486 via a pin 494, generally as described above in Example 6. The disc may have opposing faces 496, 498.

Conduit assembly 480 may incorporate a detent member 500 to lock valve 482 in the closed configuration of FIG. 20. The detent member may function to restrict valve 482 from opening accidentally and/or prematurely. The detent member may be attached to conduit 486 and may contact face 496 of the disc, for example, contacting a body 502 of disc 485 or a boss 504 projecting from the body.

Detent member 500 may have any suitable structure. For example, detent member may include a head 506 connected to a stem 508 projecting from a central region of the head. The detent member may be configured to be received at least partially in end 490 of conduit 486. In some embodiments, head 506 may include an inner portion 510 and an outer portion 512. Inner portion 510 may have a diameter less than the diameter of channel 488 of conduit 486 and may function to generally center the stem transversely in the channel. Outer portion 512, in contrast, may have a diameter that is greater than the diameter of channel 488, to restrict entry of outer portion 512 into the channel.

Detent member 500 may be attached to conduit 486 by any suitable mechanism. For example, the detent member may be attached with a clamp 514, such as a tri-clamp shown here. Alternatively, detent member may be attached to conduit 486 using at least one threaded fastener, zip tie, tape, or shrink-wrapped band, or any combination thereof, among others. The detent member may completely or only partially cover the end of channel 488, and may or may not form a fluid-tight seal with conduit 486.

Valve 482 may be controlled by an actuator 516. The actuator may be accessible from outside conduit assembly 480, to permit valve 482 to be opened manually. Manual control of valve 482 may be advantageous in some applications, such as when the desired direction of fluid transfer cannot open the valve with fluid pressure (e.g., see FIG. 22).

Actuator 516 may have any suitable structure that permits the actuator to be engaged and operated by hand to control the configuration of valve 482 and particularly the position of disc 485 with respect to conduit 486. For example, actuator 516 may include a shaft 518 connected to a user interface 520, such as a handle, button, lever, or the like. The user interface is accessible from outside conduit 486, namely, disposed outward of conduit 486 or generally at the outer surface of conduit 486. Actuator 516, which may be termed a plunger, may extend transversely to a plane defined by disc 485 and/or to a position outside the conduit through an opening 522 formed in a wall 524 of the conduit. An inner end of shaft 518 may be connected to disc 485, such as via a pivotable joint 522, a flexible region, a rigid connection, or the like. In any event, actuator 516 may be urged toward valve 482 and/or conduit 486 to open valve 482 (compare FIGS. 21 and 22).

A sealed connection 525 may be formed between actuator 516 and wall 524 of the conduit to seal opening 522 (see FIG. 20). For example, a web 526, which may be flexible, may extend from shaft 518 to wall 524, completely around the shaft, to prevent fluid flow through opening 522. The flexibility of web 526 may permit shaft 518 to move with respect to conduit 486 (e.g., compare FIGS. 21 and 22). Web 526 may be a discrete piece(s) that is secured to conduit 486 and shaft 518, or may be integral to the conduit and/or shaft.

Actuator 516 may be configured to be locked in position with respect to conduit 486, with valve 482 open, thereby locking the valve in an open configuration (compare FIGS. 21 and 22). For example, conduit assembly 480 may include a lock assembly 528 formed by actuator 516 and conduit 486. In the present illustration, lock assembly 528 includes a shroud 530, also termed a brace member, projecting from shaft 518 and also includes flanges 532 that oppposingly flank opening 522 defined by conduit 486. The shroud may be forced under flanges 532 when valve 482 is opened, to lock the shroud and thus actuator 516 in position. Shroud 530 also may function to form a cover over web 526, which may effectively increase the strength of the web, to prevent the web from bursting from an increased fluid pressure during fluid transfer. Accordingly, shroud 530 may be thicker, stronger, or more rigid than web, or any combination thereof.

FIG. 21 shows conduit assembly 480 being used in steam sterilization, with valve 482 still in the closed configuration. To provide the configuration of FIG. 21, detent member 500 may be disconnected and removed from conduit 486. Another conduit 534 may be connected to conduit 486, in place of detent member. Steam 483 then may be applied to conduit 534 and to conduit 486 up to valve 482.

FIG. 22 shows conduit assembly 480 after valve 482 has been opened manually and locked in the open configuration. Fluid reagent 484 may be flowed, also termed moved (e.g., driven), through valve 482 in either direction, such as in a direction 536 that would not open the valve if the valve were actuated strictly by fluid pressure. In particular, pressure exerted in direction 536 urges disc 485 against a seating structure 538 of the valve when the valve is closed, thereby preventing the valve from opening.

Example 8

Conduit Assembly with Upstream Port

Figure 23:
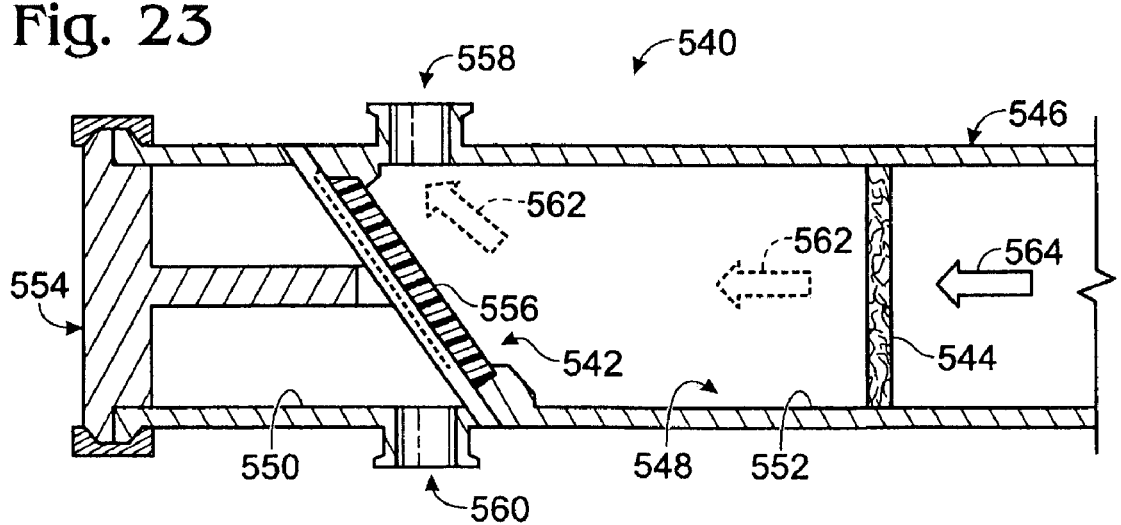
FIG. 23 is a fragmentary, longitudinal sectional view of an exemplary conduit assembly including a valve and configured to permit integrity testing of an upstream filter with the valve locked in a closed configuration using a detent member, in accordance with aspects of the present teachings.

This example describes an exemplary conduit assembly 540 including a valve 542 and configured to permit integrity testing of an upstream filter 544 with the valve in a locked configuration; see FIG. 23

Conduit assembly 540 may include a conduit 546 defining a channel 548 divided into a downstream portion 550 and an upstream portion 552 by valve 542. Here, valve 542 is a rupture valve (see Example 5). However, any other suitable valve or combination of valve features disclosed in the present teachings may be incorporated into the conduit assembly. The valve may be locked in a closed configuration by a detent member 554 (e.g., see Example 7), to prevent the valve from opening when a net pressure is exerted on an upstream face 556 of the valve during integrity testing of filter 544.

Conduit 546 may include one or more lateral ports 558, 560 that provide lateral pathways for fluid flow. In the present illustration, the lateral ports may include an upstream port 558 and a downstream port 560. The upstream port may be used to permit fluid lateral flow out of the conduit, indicated by flow arrows at 562, when a pressure 564 is exerted on filter 544. The ability of filter 544 to maintain a sufficient pressure drop, from an upstream side of the filter to a downstream side of the filter, may be used to determine whether or not the filter has lost integrity (e.g., lost the ability to efficiently remove microorganisms from fluid flowing through the filter). Accordingly, the filter integrity test may be used to determine whether or not the filter is damaged. In some embodiments, upstream port 558 may be connected to a valve, a collapsible bag, or both, among others.

Example 9

Selected Embodiments

Methods of Fluid Transfer

This example describes selected embodiments of the present teachings, related generally to methods of fluid transfer, and presented as a series of indexed paragraphs.

1. A method of fluid transfer using a conduit assembly including a conduit defining a channel and also including a valve blocking flow through the channel to divide the channel into a first portion and a second portion, the valve opening in response to pressure exerted selectively on the valve from the first portion relative to pressure exerted on the valve from the second portion, the method comprising: (A) applying steam to the second portion of the conduit with the valve restricting entry of the steam into the first portion; (B) opening the valve by applying pressure on the valve from the first portion; and (C) flowing a liquid along the conduit and through the valve after the step of opening.

2. A method of fluid transfer using a conduit assembly including a conduit defining a channel and also including a rupture valve blocking flow through the channel to divide the channel into a first portion and a second portion, the rupture valve opening selectively in response to pressure exerted on the rupture valve from the first portion relative to pressure exerted on the rupture valve from the second portion, the method comprising: (A) applying steam to the second portion of the conduit with the rupture valve restricting entry of the steam into the first portion; (B) rupturing the rupture valve to open the rupture valve using pressure exerted on the rupture valve from the first portion; and (C) causing a liquid to flow through the open rupture valve.

3. The method of paragraph 2, wherein the conduit is a first conduit, and wherein the conduit assembly includes a second conduit that branches from the first conduit, further comprising a step of removing steam condensate from the first conduit through the second conduit.

4. The method of paragraph 2, wherein the step of rupturing the rupture valve is performed volitionally.

5. The method of paragraph 2, wherein the rupture valve has a predefined hinge region at which the rupture valve bends when the rupture valve opens.

6. The method of paragraph 2, wherein the conduit assembly includes a detent member disposed in the second portion and restricting rupture of the rupture valve, further comprising a step of removing the detent member from the second portion before the step of applying steam.

7. The method of paragraph 6, wherein the rupture valve has opposing first and second faces with the first face in contact with the first portion and the second face in contact with the second portion, and wherein the step of removing the detent member includes a step of placing the detent member out of contact with the second face.

8. The method of paragraph 2, wherein the conduit assembly includes an actuator operatively coupled to the rupture valve, and wherein the step of rupturing is performed by applying pressure to the rupture valve via manual pressure transmitted by the actuator.

9. The method of paragraph 8, wherein a web connects the actuator to the conduit to form a sealed connection between the actuator and the conduit, further comprising a step of locking a brace member to the conduit over the web.

10. The method of paragraph 8, further comprising a step of locking the actuator to the conduit such that motion of the actuator with respect to the conduit is restricted after the step of applying pressure.

11. The method of paragraph 2, wherein the conduit assembly includes a filter configured to filter microorganisms and operatively coupled to the conduit such that a fluid flowing through the conduit passes through the filter, and wherein the conduit defines a port disposed between the rupture valve and the filter, further comprising a step of testing an integrity of the filter using the port for lateral flow from the conduit.

12. The method of paragraph 2, wherein the step of rupturing is performed with pressure applied by a fluid.

13. The method of paragraph 2, wherein the conduit assembly is connected to a bioreactor, and wherein the step of causing a liquid to flow includes a step of causing a medium for growing biological cells to flow through the rupture valve and into the bioreactor.

14. The method of paragraph 2, further comprising a step of connecting a vessel to the conduit assembly, wherein the vessel contains the liquid, and wherein the step of causing a liquid to flow through the open rupture valve causes at least a portion of the liquid to flow from the vessel through the rupture valve.

15. The method of paragraph 2, further comprising a step of filtering the liquid before the liquid reaches the rupture valve.

16. A method of fluid transfer using a conduit assembly including a first conduit defining a channel and a second conduit that branches from the first conduit and also including a rupture valve blocking flow through the channel to divide the channel into a first portion and a second portion, the rupture valve being selectively rupturable in response to pressure exerted on the rupture valve from the first portion relative to pressure exerted on the valve from the second portion, the method comprising: (A) applying steam to the second portion with the rupture valve restricting entry of the steam into the first portion; (B) removing steam condensate from the first conduit through the second conduit; and (C) rupturing the rupture valve with pressure exerted on the rupture valve from the first portion such that fluid flow through the rupture valve is permitted.

17. The method of paragraph 16, wherein the step of rupturing the rupture valve is performed volitionally.

18. The method of paragraph 16, wherein the rupture valve has a predefined hinge region at which the rupture valve bends when the rupture valve opens.

19. The method of paragraph 16, wherein the rupture valve has opposing first and second faces with the first face in contact with the first portion and the second face in contact with the second portion, wherein the conduit assembly includes a detent member disposed in the second portion and restricting rupture of the rupture valve, further comprising a step of removing the detent member from the second portion before the step of applying steam.

20. The method of paragraph 16, wherein the conduit assembly includes an actuator operatively coupled to the rupture valve, and wherein the step of rupturing is performed by applying pressure to the rupture valve via the actuator with the actuator engaged by hand.

21. The method of paragraph 16, further comprising a step of connecting a vessel to the conduit assembly, wherein the vessel contains a fluid reagent, further comprising a step of causing at least a portion the fluid reagent to flow from the vessel through the rupture valve.

22. A method of fluid transfer using a conduit assembly including a conduit defining a channel and also including a rupture valve blocking fluid flow through the conduit to divide the channel into first and second portions, the rupture valve having opposing first and second faces with the first face in contact with the first portion and the second face in contact with the second portion, the rupture valve opening selectively in response to pressure exerted on the first face relative to pressure exerted on the second face, the method comprising: (A) applying steam to the second portion with the rupture valve restricting entry of the steam into the first portion; and (B) opening the rupture valve volitionally with pressure exerted on the first face to permit fluid flow through the valve.

23. The method of paragraph 22, wherein the conduit assembly includes an actuator operatively coupled to the rupture valve, and wherein the step of rupturing is performed by applying pressure to the rupture valve via the actuator with the actuator engaged by hand.

Example 10

Selected Embodiments

Swing Valves

This example describes selected embodiments of the present teachings, related generally to swing valves, and presented as a series of indexed paragraphs.

1. A method of fluid transfer using a conduit assembly including a conduit defining a channel and also including a valve blocking flow through the channel to divide the channel into a first portion and a second portion, the valve including a discrete disc coupled movably to the conduit and disposed in a sealed connection with the conduit, the disc being configured to move out of the sealed connection in response to pressure exerted on the valve from the first portion, the method comprising: (A) applying steam to the second portion of the conduit with the valve restricting entry of the steam into the first portion; (B) opening the valve by moving the disc out of the sealed connection using pressure applied to the disc from the first portion; and (C) flowing a liquid through the valve after the step of opening.

2. The method of paragraph 1, wherein the step of opening the valve includes a step of pivoting the disc with respect to the conduit.

3. The method of paragraph 2, wherein the disc is coupled to the conduit such that the disc is permitted to move translationally and pivotally with respect to the conduit.

4. The method of paragraph 2, wherein the disc is coupled to the conduit using a pin received in a slot, wherein the slot defines a long axis transverse to a direction through the slot, and wherein the step of opening the valve includes a step of creating relative motion of the pin and the slot such that the pin changes position along the long axis of the slot.

5. The method of paragraph 1, wherein the sealed connection of the disc and the conduit is formed at least in part by a discrete sealing member disposed between the disc and the conduit and attached to the disc, and wherein moving the disc moves the disc and the sealing member as a unit.

6. The method of paragraph 1, wherein the disc has opposing first and second faces with the first face in contact with the first portion and the second face in contact with the second portion, and wherein the step of opening the valve includes a step of applying pressure generally at the first face using an actuator operatively coupled to the disc and with the actuator engaged by hand.

7. The method of paragraph 6, wherein a web connects the actuator to the conduit to form a sealed connection between the actuator and the conduit, wherein the actuator includes a shroud, and wherein the step of applying pressure is included in a step of moving the actuator with respect to the conduit such that the shroud moves closer to the web.

8. The method of paragraph 1, wherein the conduit assembly includes a detent member disposed in the second portion and restricting movement of the disc, further comprising a step of removing the detent member from the second portion before the step of applying steam.

9. The method of paragraph 8, wherein the valve has opposing first and second faces with the first face in contact with the first portion and the second face in contact with the second portion, and wherein the step of removing the detent member includes a step of placing the detent member out of contact with the second face.

10. The method of paragraph 1, further comprising a step of locking the valve in an open configuration such that movement of the disc is restricted.

11. The method of paragraph 1, wherein the conduit assembly includes a filter configured to filter microorganisms and operatively disposed in the conduit such that fluid flowing through the conduit passes through the filter, and wherein the conduit defines a port disposed between the rupture valve and the filter.

12. The method of paragraph 1, wherein the step of opening the valve is performed with pressure applied by a fluid.

13. The method of paragraph 1, wherein the conduit assembly is connected to a bioreactor, and wherein the step of moving a liquid includes a step of moving a medium for growing biological cells through the valve and into the bioreactor.

14. The method of paragraph 1, further comprising a step of connecting a vessel to the conduit assembly, wherein the vessel contains the liquid, and wherein the step of flowing moves at least a portion of the liquid from the vessel through the valve.

15. The method of paragraph 1, further comprising a step of filtering the liquid before the liquid reaches the valve.

16. A device for controlling fluid flow, comprising: (A) a conduit defining a channel; and (B) a valve blocking fluid flow through the channel in a closed configuration of the valve to divide the channel into first and second portions, the valve including a discrete disc movably coupled to the conduit and disposed in a sealed connection with the conduit, the disc having opposing faces and moving to provide an open configuration of the valve in response to pressure exerted on one of the opposing faces from the first channel portion relative to pressure exerted on the other opposing face from the second channel portion.

17. The device of paragraph 16, further comprising an actuator operatively coupled to the disc to permit the valve to be opened from outside the conduit through application of pressure generally to the one opposing face via the actuator engaged by hand.

18. The device of paragraph 17, wherein the valve is configured to be locked in an open configuration by manipulation of the actuator.

19. The device of paragraph 16, wherein the disc is coupled to the conduit using a pin received in a slot such that the disc is permitted to move translationally and pivotably with respect to the conduit.

20. The device of paragraph 16, further comprising a filter configured to filter microorganisms and operatively coupled to the conduit such that fluid flowing through the conduit passes through the filter.

21. The device of paragraph 16, further comprising a detent member disposed at least partly in the second portion and in contact with the other opposing face of the disc such that the valve is locked in a closed configuration until the support member is moved out of contact with the disc.

Example 11

Selected Embodiments

Manually Actuated Valves

This example describes selected embodiments of the present teachings, related generally to manually actuated valves, and presented as a series of indexed paragraphs.

1. A method of fluid transfer using a conduit assembly including a conduit defining a channel and also including a valve having opposing faces and blocking flow through the channel to divide the channel into a first portion in contact with one of the opposing faces and a second portion in contact with the other opposing face, the method comprising: (A) applying steam to the second portion of the conduit with the valve restricting entry of the steam into the first portion; and (B) opening the valve by applying pressure generally to the one opposing face using an actuator operatively coupled to the valve and engaged by hand.

2. The method of paragraph 1, further comprising a step of causing a liquid to flow through the open valve after the step of opening.

3. The method of paragraph 1, wherein a web connects the actuator to the conduit to form a sealed connection between the actuator and the conduit, wherein the actuator includes a brace member, further comprising a step of locking the brace member to the conduit over the web.

4. The method of paragraph 1, further comprising a step of locking the actuator to the conduit such that motion of the actuator with respect to the conduit is restricted.

5. The method of paragraph 1, wherein the step of opening the valve includes a step of rupturing the valve.

6. The method of paragraph 1, wherein the valve includes a discrete disc disposed in a sealed connection with the conduit, and wherein the step of opening the valve includes a step of moving the disc with respect to the conduit.

7. A device for controlling fluid flow, comprising: (A) a conduit defining a channel; (B) a valve formed in the conduit and blocking fluid flow through the channel in a closed configuration to divide the channel into first and second portions on opposing sides of the valve, the valve including opposing faces and opening to provide an open configuration of the valve selectively in response to pressure exerted on one of the opposing faces from the first portion of the channel relative to pressure exerted on the other opposing face from the second portion of the channel; and (C) an actuator disposed in a sealed connection with the conduit and operatively coupled to the valve, the actuator being accessible outside the conduit to permit a user to exert pressure generally on the one opposing face with the actuator engaged by hand, to place the valve in the open configuration manually.

8. The device of paragraph 7, wherein the actuator is configured to be locked in position with the valve in the open configuration, to restrict placement of the valve back into the closed configuration.

9. The device of paragraph 7, wherein the actuator is connected to the conduit with a web to form a sealed connection between the actuator and the conduit.

10. The device of paragraph 7, wherein the actuator includes a brace member that locks to the conduit over the web in an open configuration of the valve.

Example 12

Selected Embodiments

Removable Detent Members

This example describes selected embodiments of the present teachings, related generally to valves controlled with removable detent members, and presented as a series of indexed paragraphs.

1. A device for controlling fluid flow, comprising: (A) a conduit defining a channel; (B) a valve formed in the conduit and blocking fluid flow through the channel in a closed configuration to divide the conduit into first and second portions on opposing sides of the valve, the valve including opposing faces and opening selectively to provide an open configuration of the valve in response to pressure exerted generally on one of the opposing faces from the first conduit portion relative to pressure exerted generally on the other opposing face from the second conduit portion; and (C) a detent member received removably in the second conduit portion and disposed in engagement with the other opposing face of the valve, to hold the valve in the closed configuration.

2. The device of paragraph 1, wherein the detent member is fastened to the conduit.

3. The device of paragraph 1, wherein the channel includes opposing ends, wherein the detent member includes a stem connected to a head, wherein the stem is engaged with the other opposing face of the valve, and wherein the head covers one of the opposing ends of the channel.

4. The device of paragraph 1, wherein the channel has opposing ends, wherein the conduit defines a pair of lateral ports disposed intermediate the opposing ends and respectively providing a pathway for lateral fluid flow from the first and second conduit portions.

Example 13

Selected Embodiments

Rupture Valves

This example describes selected embodiments of the present teachings related generally to rupture valves and presented as a series of indexed paragraphs.

1. A method of fluid transfer, comprising: (A) selecting a conduit assembly including a conduit and a rupture valve dividing a channel of the conduit into an inlet portion and an outlet portion, the rupture valve being selectively rupturable in response to pressure exerted on the rupture valve from the inlet portion; (B) applying steam to the outlet portion of the conduit with the rupture valve restricting entry of the steam into the inlet portion; and (C) rupturing the rupture valve after the step of applying with pressure exerted from the inlet portion such that fluid flows into the outlet portion from the inlet portion.

2. The method of paragraph 1, further comprising a step of connecting the conduit assembly to a closed vessel before the step of applying steam.

3. The method of paragraph 2, wherein the step of connecting includes a step of connecting the conduit assembly such that the closed vessel is farther downstream from the inlet portion than the outlet portion.

4. The method of paragraph 2, further comprising a step of steaming an interior region of the closed vessel.

5. The method of paragraph 4, wherein the step of steaming is included in the step of applying steam to the outlet portion.

6. The method of paragraph 4, wherein the step of steaming is performed before the step of applying steam to the outlet portion.

7. The method of paragraph 2, further comprising a step of adding a fluid reagent to the closed vessel through the rupture valve, and wherein pressure exerted by the fluid reagent performs the step of rupturing.

8. The method of paragraph 7, wherein the closed vessel is a bioreactor, and wherein the step of adding includes a step of adding a medium for growing biological cells.

9. The method of paragraph 7, further comprising a step of connecting a source of the fluid reagent to the conduit assembly such that the outlet portion is farther downstream from the source than the inlet portion.

10. The method of paragraph 9, wherein the step of connecting a source is performed before the steps of applying and rupturing.

11. The method of paragraph 7, further comprising a step of filtering the fluid reagent as the fluid reagent is flowing to the closed vessel.

12. The method of paragraph 11, wherein the step of filtering is performed upstream of the rupture valve in the conduit assembly.

13. The method of paragraph 1, the conduit defining a long axis, wherein the step of applying is performed with the long axis disposed generally vertically.

14. The method of paragraph 1, wherein the rupture valve includes a rupturable element connected to and occluding the conduit, and wherein the step of rupturing is performed without detaching the rupturable element completely from the conduit.

15. The method of paragraph 1, the conduit being a main conduit, the conduit assembly also including an ancillary conduit that branches from the main conduit, further comprising a step of removing steam condensate from the main conduit via the ancillary conduit during the step of applying.

16. The method of paragraph 1, further comprising a step of sterilizing the conduit assembly prior to the step of applying steam.

17. The method of paragraph 16, further comprising a step of connecting the conduit assembly to an upstream device, wherein the step of sterilizing includes a step of sterilizing the conduit assembly and the upstream device as a connected unit.

18. The method of paragraph 16, further comprising a step of coupling the conduit assembly to a downstream device, wherein the step of coupling is performed before the step of applying steam.

19. The method of paragraph 18, wherein the step of coupling the conduit assembly to a downstream device is performed after the step of connecting the conduit assembly to an upstream device.

20. A device for controlling fluid flow, comprising: (A) a conduit defining a channel with opposing upstream and downstream directions of potential fluid flow; and (B) a rupture valve occluding the channel and being configured to resist rupture in response to pressure exerted on the rupture valve in an upstream direction and to rupture selectively in response to pressure exerted on the rupture valve in the downstream direction, the rupture valve being disposed obliquely in the channel.

21. The device of paragraph 20, wherein the rupture valve has a perimeter defining a plane, and wherein the plane is oblique to the directions of potential fluid flow.

22. The device of paragraph 20, wherein the conduit has a body that is at least substantially linear.

23. The device of paragraph 20, wherein the conduit is shaped at least substantially as a hollow cylinder.

24. The device of paragraph 20, wherein the conduit has a substantially circular cross-sectional shape.

25. The device of paragraph 20, wherein the conduit includes a body and opposing end regions, and where at least one of the opposing end regions includes a flange extending generally outward from the body.

26. The device of paragraph 25, wherein the flange is structured as a tri-clamp fitting.

27. The device of paragraph 20, wherein the conduit is a main conduit, further comprising an ancillary conduit branching laterally from the main conduit.

28. The device of paragraph 27, wherein the ancillary conduit includes a tri-clamp fitting.

29. The device of paragraph 27, wherein the ancillary conduit is disposed downstream of the rupture valve.

30. The device of paragraph 29, wherein the rupture valve has a downstream face disposed in a range of longitudinal positions in the conduit, wherein the ancillary conduit defines a passage, and wherein the passage has a longitudinal location along the conduit that overlaps the range of longitudinal positions.

31. The device of paragraph 30, wherein the passage at least substantially adjoins the downstream face.

32. The device of paragraph 27, wherein fluid flow through the ancillary conduit from the channel is regulated by a lateral valve that is operatively coupled to the ancillary conduit.

33. The device of paragraph 32, wherein the lateral valve is a pinch valve.

34. The device of paragraph 20, wherein the rupture valve includes a rupturable element and a support element disposed face to face with one another, wherein the rupturable element is configured to rupture selectively in response to pressure exerted in the downstream direction, and wherein the support element is configured to support the rupturable element such that rupture of the rupturable element is resisted in response to pressure exerted on the rupturable element in the upstream direction.

35. The device of paragraph 34, wherein the support element is configured to remain at least substantially fixed relative to the conduit when the rupturable element ruptures.

36. The device of paragraph 34, wherein the support element has opposing faces and wherein the support element defines a plurality of openings extending between the opposing faces.

37. The device of paragraph 34, wherein the support element is connected to the rupturable element such that the rupturable element and the support element pivot together when the rupturable element ruptures.

38. The device of paragraph 20, wherein the rupture valve is configured to remain connected to the conduit after rupture, and/or wherein the rupture valve has a predefined rupture region that is generally U-shaped.

39. The device of paragraph 20, further comprising a filter element operatively connected to the conduit and configured to sterilize fluid flowing through the conduit.

40. A device for controlling fluid flow, comprising: (A) a conduit defining a channel with opposing upstream and downstream directions of potential fluid flow; and (B) a rupture valve occluding the conduit such that fluid flow through the conduit is restricted, the rupture valve including a rupturable element and a support element connected to one another in a face-to-face relation, such that the support element supports the rupturable element against rupture in response to pressure on the rupture valve exerted in an upstream direction and pivots with the rupturable element to permit fluid flow through the channel after the rupturable element ruptures selectively in response to pressure exerted in an downstream direction.

41. The device of paragraph 40, wherein the device includes any combination of the limitations recited in paragraphs 21-39.

42. The device of paragraph 40, wherein the conduit defines a pair of cavities opposing one another across the rupture valve, and wherein the conduit projects inward into at least one of the pair of cavities to define a seating structure engaged by the support element and configured to selectively restrict movement of the support element in the upstream direction.

43. The device of paragraph 42, wherein the support element is flanked longitudinally within the conduit by the rupturable element and the seating structure.

44. The device of paragraph 40, wherein the support element has a perimeter, and wherein the rupturable element extends radially beyond the perimeter for attachment to the conduit.

45. The device of paragraph 40, wherein the rupturable element has a predefined region that is configured to be structurally weaker than other regions of the rupturable element such that the rupturable element is breached selectively in the predefined region.

The disclosure set forth above may encompass one or more distinct inventions, with independent utility. Each of these inventions has been disclosed in its preferred form(s). These preferred forms, including the specific embodiments thereof as disclosed and illustrated herein, are not intended to be considered in a limiting sense, because numerous variations are possible. The subject matter of the inventions includes all novel and nonobvious combinations and subcombinations of the various elements, features, functions, and/or properties disclosed herein.

The invention claimed is:

1. A method of fluid transfer using a conduit assembly including a conduit defining a channel and also including a rupture valve dividing the channel into an inlet portion and an outlet portion, the rupture valve having an inlet side and an outlet side, the method comprising:
   applying steam to the outlet portion of the channel with the rupture valve restricting entry of the steam into the inlet portion;
   rupturing the rupture valve by increasing a pressure exerted on at least a portion of the inlet side of the rupture valve to create a passageway through the rupture valve; and
   adding a fluid reagent to a receiver vessel connected to the conduit assembly, from a supply vessel containing the fluid reagent and through the passageway of the rupture valve.

2. The method of claim 1, wherein the step of adding a fluid reagent includes a step of adding a fluid reagent that is substantially liquid.

3. The method of claim 1, wherein the step of rupturing includes a step of exerting pressure on the rupture valve via gas disposed downstream of the fluid reagent in the inlet portion.

4. The method of claim 1, wherein the step of rupturing includes a step of exerting pressure on the rupture valve directly with the fluid reagent.

5. The method of claim 1, further comprising a step of connecting the conduit assembly to the receiver vessel.

6. The method of claim 5, wherein the step of connecting includes a step of connecting the conduit assembly such that the receiver vessel is farther downstream from the inlet portion than the outlet portion.

7. The method of claim 5, wherein the receiver vessel is a bioreactor, and wherein the step of adding a fluid reagent includes a step of adding a medium for growing biological cells.

8. The method of claim 1, wherein the conduit is a main conduit, wherein the conduit assembly also includes an ancillary conduit that branches from the main conduit, further comprising a step of removing steam condensate from the main conduit via the ancillary conduit during the step of applying steam.

9. The method of claim 1, wherein the conduit assembly includes a filter operatively connected to the conduit, further comprising a step of filtering the fluid reagent to remove microorganisms from the fluid reagent during the step of adding.

10. The method of claim 1, further comprising a step of sterilizing the inlet portion of the channel prior to the step of applying steam.

11. A method of fluid transfer using a conduit assembly including a main conduit defining a channel and also including an ancillary conduit that branches from the main conduit, the conduit assembly further including a rupture valve dividing the channel into an inlet portion and an outlet portion, the method comprising:

applying steam to the outlet portion of the channel with the rupture valve restricting entry of the steam into the inlet portion;

removing steam condensate from the main conduit via the ancillary conduit during the step of applying steam; and rupturing the rupture valve with pressure exerted on the rupture valve from the inlet portion to create a passageway through the rupture valve for fluid flow.

12. The method of claim 11, further comprising a step of connecting the conduit assembly to a receiver vessel and a step of adding a fluid reagent to the receiver vessel through the rupture valve.

13. The method of claim 12, wherein the step of connecting includes a step of connecting the conduit assembly such that the receiver vessel is farther downstream from the inlet portion than the outlet portion.

14. The method of claim 12, wherein the receiver vessel is a bioreactor, and wherein the step of adding a fluid reagent includes a step of adding a medium for growing biological cells.

15. The method of claim 12, further comprising (1) a step of connecting the conduit assembly to a supply vessel containing a fluid reagent, and (2) a step of adding the fluid reagent to the receiver vessel through the rupture valve after the step of rupturing.

16. The method of claim 15, wherein the conduit assembly includes a filter operatively connected to the conduit, further comprising a step of filtering the fluid reagent upstream of the rupture valve in the conduit assembly.

17. The method of claim 11, further comprising a step of sterilizing the conduit assembly prior to the step of applying steam.

18. A method of fluid transfer using a conduit assembly including a conduit defining a channel and also including a rupture valve dividing the channel into an inlet portion and an outlet portion, the rupture valve having an inlet side and an outlet side, the method comprising:

applying steam to the outlet portion of the channel with the rupture valve restricting entry of the steam into the inlet portion;

rupturing the rupture valve by increasing a pressure exerted on at least a portion of the inlet side of the rupture valve to create a passageway through the rupture valve; and flowing a fluid reagent through the passageway of the rupture valve.

19. The method of claim 18, wherein the step of flowing a fluid reagent includes a step of flowing a fluid reagent that is substantially liquid.

20. The method of claim 18, further comprising a step of sterilizing the inlet portion of the channel prior to the step of applying steam.

* * * * *